United States Patent [19]
Quick et al.

[11] Patent Number: 5,861,160
[45] Date of Patent: Jan. 19, 1999

[54] *ISOSPORA SUIS* SPOROZOITE ANTIGEN

[75] Inventors: Douglas P. Quick, DesMoines; Mark W. Welter, Urbandale; C. Joseph Welter, DesMoines, all of Iowa; Lisa M. Welter, Los Angeles, Calif.; Ann M. Steger, DesMoines, Iowa

[73] Assignee: Ambico, Inc., Dallas Center, Iowa

[21] Appl. No.: 541,759

[22] Filed: Oct. 10, 1995

Related U.S. Application Data

[63] Continuation-in-part of Ser. No. 476,401, Jun. 7, 1995, abandoned.

[51] Int. Cl.$^6$ .......................... A61K 39/002; C12P 21/02; C07K 14/44
[52] U.S. Cl. ..................................... 424/191.1; 424/269.1; 435/69.3; 435/947; 530/324; 530/350; 530/806; 530/822; 930/210
[58] Field of Search ................................... 435/69.3, 947; 424/191.1, 269.1; 530/300, 324, 350, 806, 822; 930/210

[56] References Cited

U.S. PATENT DOCUMENTS

| | | | |
|---|---|---|---|
| 4,438,097 | 3/1984 | Shirley | 424/88 |
| 4,639,372 | 1/1987 | Murray et al. | 424/88 |
| 4,650,676 | 3/1987 | Schenkel et al. | 424/88 |
| 4,724,145 | 2/1988 | Murray et al. | 424/88 |
| 4,874,705 | 10/1989 | Andrews et al. | 435/252.33 |
| 5,122,471 | 6/1992 | Jenkins et al. | 435/69.3 |
| 5,273,901 | 12/1993 | Jacobson et al. | 435/243 |
| 5,279,960 | 1/1994 | Anderson et al. | 435/243 |

FOREIGN PATENT DOCUMENTS

| | | |
|---|---|---|
| 0167443 | 1/1986 | European Pat. Off. . |
| 0231537 | 8/1987 | European Pat. Off. . |
| 0519547 | 12/1992 | European Pat. Off. . |
| 9000403 | 1/1990 | WIPO . |
| 9204460 | 3/1992 | WIPO . |
| 9216627 | 10/1992 | WIPO . |

OTHER PUBLICATIONS

Lewin, 1987. Science 237:1570.

Gmachl et al., 1990. Dermal Glands of *Xenopus laevis*. . . FEBS Lett. 260:145–8. Swiss–Prot 31 Database entry, #P17434;Q089440.

Maurer et al., 1980. Proteins and Polypeptides as Antigens. Meth Enzymol. 70:49–70.

American Journal Of Veterinary Research, vol. 52, No. 3, Mar. 1991, pp. 471–473, XP000601601 D.S. Lindsay Et Al.: "Ultrastructure of developing *Isospora suis* in cultured cells".

Doran, *Eimeria tenella: From Sporozoites to Oocysts in Cell Culture*, Proceedings of the Helminthological Society of Wash., vol. 37, No. 1, pp. 84–92, Jan. 1970.

Fayer, et al., *Isospora suis: Development in Cultured Cells with Some Cytological Observations*, Proc. Helminthol. Soc. Wash., vol. 51, No. 1, pp. 154–159, 1984.

Laurent, et al., *The immunodominant Eimeria acervulina sporozoite antigen previously described as p160/p240 is a 19–kilodalton antigen present in several Eimeria species*, Mol. Biochem. Para., vol. 63, pp. 79–86, 1994.

(List continued on next page.)

*Primary Examiner*—James C. Housel
*Assistant Examiner*—James L. Grun
*Attorney, Agent, or Firm*—William M. Blackstone

[57] ABSTRACT

*Isospora suis* is propagated using a swine testicular cell line which facilitates production of sporozoites and merozoites, either or both of which can be used in a vaccine for swine. Antibodies against *Isospora suis* sporozoites, which inhibit the infectivity of the sporozoites for the swine testicular cells, were made. These neutralizing antibodies were used to identify an apparent sporozoite attachment protein and cloned cDNA encoding a portion of the protein. The cloned cDNA was sequenced and the corresponding amino acid sequence of the antigenic sporozoite protein revealed two areas having repeated amino acid sequences, which may likewise be used in a vaccine.

5 Claims, 6 Drawing Sheets

FIRST REPEAT

| | | | |
|---|---|---|---|
| 288 | LPPTEEVPPTEEVTPPTEGETPPAEGE | 314 | SEQ ID NO:3 |
| 315 | LPPTEEVPPTEEVTPPTEGETPPTEGE | 341 | SEQ ID NO:4 |
| 342 | LPPTEEVPPTEEVTPPTEGETPPTEGE | 368 | SEQ ID NO:4 |
| 369 | LPPTEEVPPTEEVTPPTEGETPPTEGE | 395 | SEQ ID NO:4 |
| 396 | VPPTEEVPPTEEVTPPTEGETPPTEGG | 422 | SEQ ID NO:5 |
| Consensus | LPPTEEVPPTEEVTPPTEGETPPTEGE | | SEQ ID NO:4 |

SECOND REPEAT

| | | | |
|---|---|---|---|
| 430 | LHPQKAKLPRPKESCLQQRRFLPLRKS | 456 | SEQ ID NO:6 |
| 457 | LRQQRARLPRPKESCLQQRRFLPLRKS | 483 | SEQ ID NO:7 |
| 487 | LRQQRARLPRPKESCHQQRRFLPLKKS | 510 | SEQ ID NO:8 |
| 511 | LRQQRARLPRPKESFLQQRRYLPLKKS | 537 | SEQ ID NO:9 |
| Consensus | LRQQRARLPRPKESCLQQRRFLPLKKS | | SEQ ID NO:10 |

OTHER PUBLICATIONS

Lindsay, et al., *Complete Development of Isospora suis of Swine in Chicken Embryos*, J. Protozool., vol. 31, No. 1, pp. 152–155, 1984.

Lindsay, et al., *Biology of Mammalian Isospora*, Parasitology Today, vol. 10, No. 6, pp. 214–220, 1994.

Lindsay, et al., *Development of Isospora suis from Pigs in Primary Porcine and Bovine Cell Cultures*, Veterinary Parasitology, vol. 24, pp. 301–304, 1987.

Reduker, et al., *Proteins and Antigens of Merozoites and Sporozoites of Eimeria Bovis (Apicomplexa)*, J. Parasit., vol. 72, No. 6, pp. 901–907, 1986.

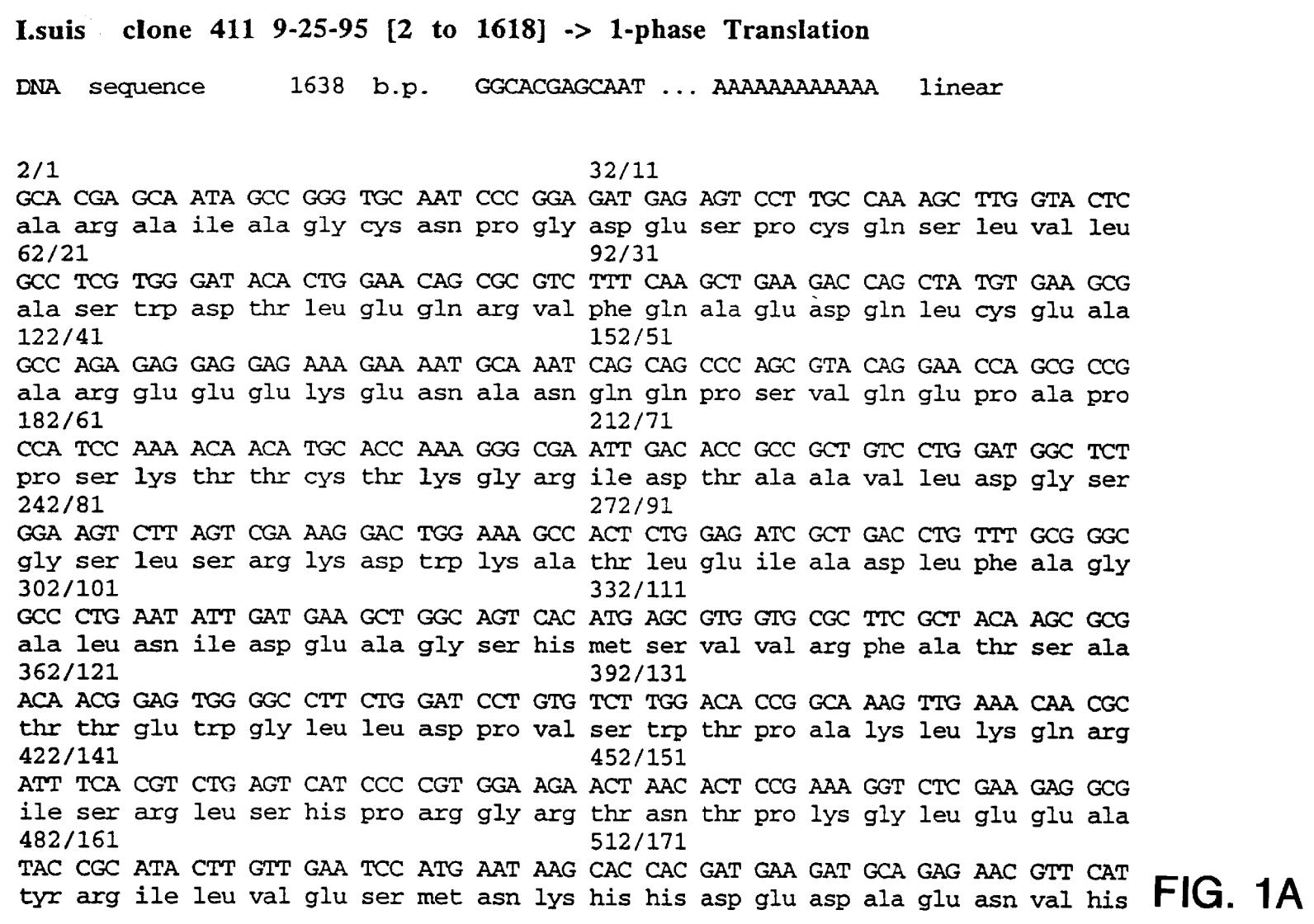

I.suis clone 411 9-25-95 [2 to 1618] -> 1-phase Translation

DNA sequence    1638 b

FIG. 1B

I.suis clone 411 9-25-95 [2 to 1618] -> 1-phase Translation

DNA sequ

FIG. 1C

I.suis clone 411 9-25-95 [2 to 1618] -> 1-phase Translation

DNA s

FIRST REPEAT

```
288 LPPTEEVPPTEEVTPPTEGETPPAEGE 314    SEQ ID NO:3
315 LPPTEEVPPTEEVTPPTEGETPPTEGE 341    SEQ ID NO:4
342 LPPTEEVPPTEEVTPPTEGETPPTEGE 368    SEQ ID NO:4
369 LPPTEEVPPTEEVTPPTEGETPPTEGE 395    SEQ ID NO:4
396 VPPTEEVPPTEEVTPPTEGETPPTEGG 422    SEQ ID NO:5
Consensus LPPTEEVPPTEEVTPPTEGETPPTEGE       SEQ ID NO:4
```

SECOND REPEAT

```
430 LHPQKAKLPRPKESCLQQRRFLPLRKS 456    SEQ ID NO:6
457 LRQQRARLPRPKESCLQQRRFLPLRKS 483    SEQ ID NO:7
487 LRQQRARLPRPKESCHQQRRFLPLKKS 510    SEQ ID NO:8
511 LRQQRARLPRPKESFLQQRRYLPLKKS 537    SEQ ID NO:9

Consensus LRQQRARLPRPKESCLQQRRFLPLKKS       SEQ ID NO:10
                                 R
```

FIG. 2

ISOSPORA SUIS SPOROZOITE ANTIGEN

This application is a continuation-in-part of Ser. No. 08/476,401, filed Jun. 7, 1995, now abandoned, which is hereby incorporated by reference.

BACKGROUND OF THE INVENTION

1. Field of the Invention

The present invention is directed to a vaccine and method of making a vaccine for *Isospora suis* based upon recombinantly derived sporozoite protective antigens, recombinantly derived merozoite protective antigens, and/or cell cultured derived merozoites.

2. Description of the Background Art

*Isospora suis* and *Swine Coccidiosis*

Coccidiosis was first reported in swine as early as 1878. However, the causative agent of this disease was not identified as *Isospora suis* until 1934. *Isospora suis* cost swine producers in the U.S. an estimated $101,000,000 from July, 1992 to May, 1993. This amounts to a loss of more than $1 billion to swine producers in the U.S. over the last ten years, assuming that the infection rates have not varied significantly. There is no current vaccine on the market, no coccidiostats are licensed for swine use, non-licensed coccidiostats have not been effective, and there has been no reported method to produce the complete life cycle of this organism outside the pig.

*Isospora* are, with few exceptions, parasites of the gastrointestinal tract. *Isospora*, as members of the genus *Eimeriidae*, are usually monoxenous, i.e., use only one host, although some species of *Isospora* have been shown to use transport hosts.

Neonatal porcine coccidiosis is caused by *Isospora suis*. Naturally infected piglets develop diarrhea 5–10 days after birth, become dehydrated, and lose weight. Morbidity is high and mortality is usually low to moderate. Lesions of villous atrophy, villous erosion, and fibrinonectroic enteritis have been described from experimentally and naturally infected piglets. The majority of clinical cases of *Isospora suis* are observed in pre-weaned pigs, with about one third of the cases occurring in post-weaned pigs. Infections are less severe in older pigs than in piglets.

Isospora are parasites of the intestinal tract and have an obligate intracellular merogony and gametogony, single host life cycle, extra-intestinal sporogony, and oocysts with two sporocysts, each of which contains four sporozoites.

Upon ingestion of the sporulated oocysts, the motile infective stages, the sporozoite, are released and enter a host cell. The sporozoites differentiate into meronts and initiate the first multiplication cycle (merogony), which is asexual. Nuclear division and growth produce multiple merozoites from a meront, the number of which depends on the species of the organism. The meront ruptures the cell and the released motile merozoites invade new host cells to initiate a second generation of meronts. In *Isospora suis*, Type-1 meronts are binucleate and divide to form two merozoites, while type-2 meronts are multinucleate and divide to form many type-2 merozoites. Merogony continues for several generations, usually two to three. Eventually the released merozoites produce the sexual stages. Some merozoites become microgamonts in which multiple nuclear divisions take place and many microgametes are formed. Other merozoites form macrogametes, which have one nucleus that does not divide. A macrogamate is fertilized by one microgamete to form a zygote. A wall of one or more layers develops around the zygote to form an oocyst, which is released into the lumen of the host's gut and excreted in the feces. Outside the body the oocyst sporulates into the infective stage. Once the oocysts are excreted from an infected animal, reduction division comes into play. The sporulation of the oocysts takes place after the oocysts have been shed from the animal. Sporulation is dependent upon temperature. The first observable nuclear division occurs at the time the sporont divides to form two spherical sporoblasts. Nuclear division occurs again and the nuclei migrate to the poles of the developing sporocysts. As a result of a final nuclear division, four sporozoites are produced in each sporocysts.

Excystation occurs in the newly infected host and is the process by which sporozoites are released from sporocysts and eventually from the oocysts. Excystation of oocysts will occur in almost any animal, but the released sporozoites will fail to produce infection in any but the normal hosts. According to several workers, excystation is a two-step process. First, the oocyst wall must be altered to make it permeable to bile and pancreatic enzymes. This is thought to be accomplished by stomach acids and in the reducing environment of the stomach. The bile and pancreatic enzymes in the intestine are thought to cause activation of sporozoites and dissolution of the Stieda body. The sporozoites leave the sporocysts through the opening left by the disintegration of the Stieda body and leave the oocysts through breaks or gaps that develop in the oocysts wall. Isospora that lack a Stieda body excyst by collapse of the sporocyst wall along plate-like junctions. The collapse releases the sporozoites into the oocysts, from which they then escape.

The Vertebrate Immune System

The ability of vertebrates to protect themselves against infectious microbes, toxins, viruses, or other foreign macromolecules is referred to as immunity. The art distinguishes between natural, and acquired or specific immunity. Natural immunity is comprised of defense mechanisms which are active before exposure to microbes or foreign macromolecules, are not enhanced by such exposure, and do not distinguish among most substances foreign to the body. Acquired or specific immunity comprises defense mechanisms which are induced or stimulated by exposure to foreign substances.

In vertebrates, the mechanisms of natural and specific immunity cooperate within a system of host defenses, the immune system, to eliminate foreign invaders. The events by which the mechanisms of specific immunity become engaged in the defense against invading microorganisms cancer cells, etc. are termed immune responses. Vertebrates have two basic immune responses: humoral and cellular. Humoral immunity is provided by B lymphocytes, which, after proliferation and differentiation, produce antibodies which circulate in the blood and lymphatic fluid. Cellular immunity is provided by the T cells of the lymphatic system. The cellular immune response is particularly effective against fungi, parasites, intracellular viral infections, cancer cells and foreign matter, whereas the humoral response primarily defends against the extracellular phases of bacterial and viral infections.

An "antigen" is a foreign substance which is recognized (specifically bound) by an antibody or a T-cell receptor, regardless of whether it can induce an immune response. Foreign substances inducing specific immunity are termed "immunizing antigens", or "immunogens". An "hapten" is an antigen which cannot, by itself, elicit an immune response (though a conjugate of several molecules of the hapten, or of the hapten to a macromolecular carrier, might do so).

The immune system has evolved so that it is able to recognize surface features of macromolecules that are not normal constituents of the host. A foreign molecule which is recognized by the immune system (e.g., bound by antibodies), regardless of whether it can itself elicit is called an "antigen", and the portion of the antigen to which an antibody binds is called the "antigenic determinant", or "epitope". When the antigen is a polypeptide, it is customary to classify epitopes as being linear (i.e., composed of a contiguous sequence of amino acids along the polypeptide chain) or nonlinear (i.e., composed of amino acids brought into proximity as a result of the folding of the polypeptide chain). (The nonlinear epitopes are also called "conformational" because they arise through the folding of the polypeptide chain into a particular conformation.)

To cope with the immense variety of epitopes encountered, the immune system of a mammalian individual contains an extremely large repertoire of lymphocytes. Each lymphocyte clone of the repertoire contains surface receptors specific for one epitope. It is estimated that the mammalian immune system can distinguish at least $10^8$ distinct antigenic determinants.

An initial or primary immune response to a foreign antigen enhances the ability of the immune system to respond again to that antigen (in a secondary immune response). This feature of specific immunity is called immunologic memory. Secondary immune responses are often more effective than primary responses.

Lymphocytes are the agents of antigenic specificity in the immune response. They can be divided into two groups. One group, the "B-lymphocytes" or "B-cells", play a central role in the production of antibodies. Antibodies (immunoglobulins, Ig's) are proteins capable of binding antigens, and exerting effector functions that are involved in the elimination of foreign antigens. The other group consists of T-lymphocytes or T-cells that perform a variety of functions including help for B-cells, production of delayed-type hypersensitivity reactions, and specific killing of virus-infected cells.

Normally, immune responses progress toward effector mechanisms characteristic of both B and T-lymphocytes. However, in the course of most immune responses, either B or T lymphocytes assume a dominant role, with less substantial participation of the respective other type of lymphocyte. Immune responses whose effector mechanisms are mediated preponderantly through B-cells and antibodies are termed humoral immune responses. Those responses wherein T-cells mediate the more important effector functions are referred to as cell-mediated or cellular immune responses.

B-cells constitute the population of lymphocytes central to humoral immune responses. Each clone of B-lymphocytes expresses membrane immunoglobulins (membrane Ig's, surface-bound antibody molecules) that function as antigen receptors with one unique epitope specifically per. B-lymphocyte clone. These membrane Ig molecules (antigen receptors) are the sole source of B-cell specificity. Antigens that contain an epitope complementary to the membrane Ig will bind to the antigen receptor. Such antigens are also referred to as cognate antigens of the antibody. On protein antigens, antibodies can bind linear determinants (epitopes formed by adjacent amino acid residues in the covalent sequence), or conformational determinants, which are formed by amino acid residues from separate portions of the linear polypeptide that are specially juxtaposed by polypeptide folding. Binding to the antigen receptor (membrane Ig) will result in differentiation and clonal proliferation of the B-lymphocyte. Some of its progeny will differentiate into mature plasma cells which are specialized in the synthesis of antibodies corresponding in epitope specificity to the membrane Ig by which the B-lymphocyte had initially bound the antigen.

By an effector mechanism typical of humoral immune responses, antibodies will bind to cognate epitopes on the surface of invading target cells, e.g., bacteria. Following antibody binding, the components of the complement system will sequentially attach to the target cell-antibody complex, resulting ultimately in the rupture of the target cell membrane and killing of the target cell. By another antibody-mediated effector mechanism, target antigens are bound and cross-linked (opsonized) by antibodies, and are thus prepared for ingestion and subsequent destruction by phagocytes of reticuloendothelial origin, such as granulocytes or macrophages.

The antibody itself is an oligomeric molecule, classified, according to its structure, into a class (e.g., IgG) and subclass (e.g., IgGl). IgG molecules are the most important component of the humoral immune response and are composed of two heavy (long) and two light (short) chains, joined by disulfide bonds into a "Y" configuration. The molecule has both variable regions (at the arms of the "Y") and a constant region (the hinge and base of the "Y"). The regions are so named because antibodies of a particular subclass, produced by a particular individual in response to different antigens, will differ in the variable region but not in the constant region. The variable regions themselves are composed of both a relatively invariant framework, and of hypervariable loops, which confer on the antibody its specificity for a particular epitope. An antibody binds to an epitope of an antigen as a result of molecular complementarity. The portions of the antibody which participate directly in the interaction is called the "antigen binding site", or "paratope". The antigens bound by a particular antibody are called its "cognate antigens".

Surface IgM is the first antibody to appear on the surface of B cells, and secreted IgM is the major component of the primary immune response. The affinity of IgM antibodies is relatively low, but this is offset by their multivalency. They are particularly effective against polyvalent antigens. IgM antibodies are very effective in inhibiting pathogens by agglutination (via complement fixation).

IgG antibodies are the major component of the secondary immune response to T dependent antigens. Certain subclasses of IgG antibodies can activate complement. Some subclasses are transferred, by specific receptors, across the placenta. IgG antibodies can also sensitize targets to eosinophils.

IgA antibodies are the major immunoglobulin component of secretions, and are transported across epithelia, aiding the body's exterior defenses.

IgE antibodies link the immune system to inflammatory effectors.

An antibody of one animal will be seen as a foreign antigen by the immune system of another animal, and will therefore elicit an immune response. Some of the resulting antibodies will be specific for the unique epitopes (idiotype) of the variable region of the immunizing antibody, and are therefore termed anti-idiotypic antibodies. These often have immunological characteristics similar to those of an antigen cognate to the immunizing antibody. Anti-isotypic antibodies, on the other hand, bind epitopes in the constant region of the immunizing antigen.

The typical effector phase of cell-mediated or cellular immune responses involves lysis or killing of target cells by cytotoxic or cytolytic T-lymphocytes (CTLs) through direct cell-to-cell contact. Molecules from two diverse families of cell-surface glycoproteins, the T-cell receptors (TCRs) and the major histocompatibility complex (MHC) type I glycoproteins, are the key elements of specificity in the CTL response to foreign antigens. T-cell receptors (TCRs) recognize short, linear peptide determinants of 8–24 amino acids, the generation of which usually requires unfolding and proteolytic fragmentation ("processing") of the antigenic protein. They can also recognize oligosaccharide determinants. Unlike antibodies, T-cell receptors cannot recognize conformational epitopes.

The second difference in antigen recognition by antibodies and T-cell receptors is the involvement of a third molecule that performs the role of presenting the antigen to the T-cell receptor. For B-cells, such molecules are not necessary, as the membrane Ig (antibody) forms a stable bimolecular complex with the antigenic protein. For T-cells, the antigenic peptide must be bound by an MHC glycoprotein, and it is this complex of MHC molecule plus peptide that forms the structure recognized by the T-cell receptor. MHC glycoproteins are thus peptide-binding proteins which function as antigen-presenting molecules.

Poultry Coccidiosis (*Eimeria*) Vaccines

While the art has not developed a vaccine against *Isospora suis*, the cause of coccidiosis in pigs, the poultry coccidiosis agents, which are various species of the genus *Eimeria*, have proven to be more tractable.

*Eimeria necatrix* has been attenuated by inoculating sporozoites into embryonated eggs, passaging 20–60 times, and then harvesting oocysts. An oocyst suspension can then be used as a live vaccine against coccidiosis in poultry. See Shirley, U.S. Pat. No. 4,438,097.

Sporozoites have been isolated from oocysts and used directly as vaccines. Bhogal, et al. U.S. Pat. No. 5,068,104, teaches keeping *Eimeria* sporozoites alive, after emergence, by encapsulating them. The microcapsulated sporozoites are administered to baby chicks.

Murray, EP 167,443 (Merch & Co.) and U.S. Pat. No. 4,639,372 suggests that extracts from sporozoites or sporulated oocysts of *Eimeria tenella*, which do not contain viable or intact parasites, can be used to protect chickens from coccidiosis. According to Murray, these extracts "contain at least 15 polypeptides, many of which are associated with the surface of the sporozoite and induce good immune responses." In Murray, U.S. Pat. No. 4,724,145, similar use is made of an *E. acervulina* extract to protect against *E. acervulina*, *E. tenella*, and *E. maxima*.

There has been considerable interest in producing particular *Eimeria* sporozoite antigens by recombinant DNA techniques, as summarized below:

| | |
|---|---|
| 25 kDa *E. acervulina* antigen ac-1b; 21.6 kDa *E. accervulina* antigenic fragment ac-6b; 16.6 kDa *E. tenella* antigen tc-7a; 3.5 kDa *E. tenella* antigenic fragment tc-89; 7.8 kDa *E. tenella* antigenic fragment tc-10a, all immunoreactive with anti-sporozoite monoclonal antibodies | Jacobson U.S. Pat. No. 5,273,901 and WO92/04460 |
| 25 kDa *E. tenella* antigen | Anderson U.S. Pat. No. 5,279,960 and WO90/00403 |
| 25 kDa *E. tenella* antigen composed of two disulfide bonded polypeptides (12 and 8 kDa). | Andrews, U.S. Pat. No. 4,874,705 and Newman EP 231,537 (Solvay) |
| 50–65 kDa *E. maxima* antigen | Harwood, WO92/16627 (Campbell Soup) |
| 100 kDa *E. acervulina* antigen | Kok, EP 519,547 (Akzo) |

Kok also identified 20, 45, 100 and 200 kDa *E. acervulina* merozoite antigens. Schenkel, U.S. Pat. No. 4,650,676 discussed 300±50, 130±20 and 18±3 kDa merozoite antigens.

Comparison of *Isospora* and *Eimeria*

*Isospora* and *Eimeria* are genera which contain parasites which are similar in many respects but different in other, significant respects. Both cause coccidiosis in warm-blooded animals, and, in general, the route of infection, the general reproductive cycle, and clinical diseases caused by *Isospora* and *Eimeria* are also similar. However, *Isospora suis* is only known to reproduce itself in swine and is the only pathogen to cause coccidiosis in pigs, while *Eimeria* species have been observed in a wide variety of animals while not necessarily causing disease in these animals. *Eimeria* species have been observed in swine while not necessarily causing disease in swine, and can cause disease in avians, including chickens and turkeys.

Because of this difference in hosts, the immune response to an *Isospora suis* infection differs from that to an infection caused by *Eimeria*. The immune response of birds is quite different from that of pigs in many respects, including mechanisms of preventing or limiting coccidial infections.

Birds have a bursa where B-cells are known to differentiate, and pigs do not have a bursa. The bursa equivalent in swine for the mucosal system is understood to be in the intestines (American Society of Biochemist and Molecular Biologist convention in San Francisco, Calif., in January, 1989). The digestive and reproductive systems are also very different. These differences inhibit the direct application of chicken *Eimeria* research to swine *Isospora suis* vaccine development.

The antigens presented by the two genera are also different. The immunodominant *Eimeria acervulina* sporozoite antigen (previously described as p160/p240) is a 19 kilodalton antigen present in several *Eimeria species* (cf. Laurent et al. in *Mol. Biochem. Parasit.* 63: 79–86, 1994), while that of *Isospora suis* is 207 and 218 kilodaltons. *Eimeria bovis* have merozoite surface proteins with molecular weights between 15 and 18 kD, and have sporozoite surface proteins of 28, 77 and 183 kD (cf. Reduker et al., *J. Parasit.* 72(6): 901–907, 1986), while *Isospora suis* does not.

*Isospora* species are in general more difficult to work with than *Eimeria* species for the following reasons:

(a) fewer oocysts are produced;

(b) more fat is present in mammalian diets than in avian diets, making purification of oocysts more difficult;

(c) the oocyst wall is thinner in *Isospora* than *Eimeria*, making it more difficult to sterilize and store;

(d) mammalian hosts not previously exposed to *Isospora* are more difficult to find and more costly to purchase than the *Eimeria* avian hosts (cf. Lindsay et al., *Parasitology Today*, 10(6): 214–220, 1994).

The conventional belief is that it is not possible to confer passive immunity to *Isospora suis*. Baekbo et al., Proceeding of the 13th IPVS Congress, Bangkok, Thailand, 26–30 June, 1994, state, "With the set-up in the present experimental study it was impossible to transfer a passive protective immunity against *I. suis* infection from sows to their offspring."

Development of *Isospora Suis* in Cell Culture and in Embryos

Lindsay and Current, J. Protozool., 31:152–5 (1984) reported the "complete" development of *Isospora suis* in chicken embryos. The allantoic cavities were inoculated with sporozoites. The authors obtained Type 1 meronts and merozoites, Type 2 meronts and merozoites, and mature microgamonts, macrogamonts, and oocysts. However, sporulation did not occur. The disadvantages of an embryo system include the following: (a) the yield of merozoites and oocysts is very low; (b) The oocysts are not viable (alive); and (c) The use of eggs for vaccine production is more labor intensive and would require safety testing for viruses that may be present in the embryos.

Fayer, et al., Proc. Helminthol. Soc. Wash., 51:154–9 (1984) described an unsuccessful effort to induce intracellular development of sporozoites inoculated into Madin-Darby bovine kidney (MDBK), embryonic bovine trachea (EBTr), bovine colon (BC) and porcine kidney (PK) cell cultures.

Lindsay and Blagburn, Veter. Parasitol., 24:301–4 (1987) inoculated primary porcine kidney (PPK) and fetal bovine kidney (PFBK) cell cultures with sporozoites of *Isospora suis*. Motile merozoites and binucleate Type I meronts were observed in both cultures. Multinucleate Type II meronts, which did not form merozoites, developed in PPK cell cultures only.

Lindsay and Blagburn, Parasitol. Today, 10:214 (1994) summarized the then state of the art as follows:

several mammalian *Isospora* species have been grown in cell cultures . . . with several divisions occurring by endodyogeny. Only *I. rivolta* and *I. suis* have produced multinucleate (more than two nuclear) schizonts in cell cultures and these schizonts did not reach maturity. Sexual stages and oocysts have not developed in cell cultures. Continuous cultivation of an *Isospora* species has not been achieved.

In contrast, with *Eimeria*, more than two decades earlier, the art had discovered how to progress from sporozoites to functional oocysts in cell culture. See Doran, Proc. Helminth. Soc., 37:84 (1970).

SUMMARY OF THE INVENTION

The present invention provides a method for producing an *Isospora suis* vaccine using both cell culture and recombinant technologies. Cell culture technologies are used for producing merozoite antigens and sexual stage antigens. Recombinant technologies are used to produce sporozoite antigens, and optionally, merozoite and/or sexual stage antigens.

In one aspect, the invention relates to the production of large numbers of merozoites by inoculating sporozoites into a culture of swine testicular cells. Primary pig kidney, primary dog kidney, established MDBK, established bovine turbinate and established swine testicular cells were grown to confluency and inoculated with the same number of sporozoites. Free swimming merozoites were observed in all of the cell cultures, but the swine testicular cells had from ten to twenty times as many free swimming and intracellular merozoites. Thus, while merozoites have been produced before in cell culture, the present invention provides a much more efficient process for merozoite production, which in turn facilitates production of a vaccine comprising merozoite antigens. Both type 1 and type 2 merozoites were produced, as well as oocysts.

The present inventors have also established that merozoites derived from swine testicular culture are infectious and virulent in pigs. This verifies that the cell culture derived merozoites have not been dramatically altered in infectious capability by passage through swine testicular cells from the native pig derived merozoites.

Cell culture derived merozoites can be used for oral and/or intramuscular vaccination of gilts, which significantly reduces the mortality of nursing piglets which had been challenged with sporulated *Isospora suis* oocysts. These cell culture derived merozoites can be used to make an effective vaccine for nursing piglets as well as for adult pigs.

In another aspect, the invention relates to a neutralizing monoclonal antibody. Serum neutralizing(SN) antibodies are antibodies which inhibit the infection of a pathogen into the target cell they normally invade. The presence of these antibodies at a neutralizing titer at the surface of the target cell substantially interferes with infection of the pathogen's target cells. The neutralizing titer is the lowest concentration of antibody which results in a significantly reduced infection. Thus, if a vaccine results in the production of neutralizing titers of antibodies at the surface of the target cell, a significantly reduced infection of the target cells (relative to controls) will take place, at a given challenge level of the pathogen.

This antibody has been shown to inhibit the infection of swine testicular cells by sporozoites. This antibody has several utilities. First, it can be used in immunoassays for *Isospora suis* sporozoites, or for serum antibodies elicited by the presence of sporozoites. These assays are particularly useful in identifying and titrating IgA antibodies in the milk which correlate to protection of the pigs. Second, the antibody can be used to passively protect piglets from coccidiosis. Third, the antibody may be used to immunopurify cognate sporozoite antigens for use as vaccines. Finally, the antibody may be used in the immunoscreening of a sporozoite cDNA expression library to aid in the identification of cDNA encoding the recognized antigen. Two polyclonal antisera, specific, respectively, for merozoites and sporozoites, have also been developed, and may be used in an analogous manner.

We have demonstrated that sporozoites can be inhibited from infecting ST cells by specific polyclonal and monoclonal antibody. We have demonstrated that neutralizing antibodies are present in the milk of vaccinated sows which protect nursing piglets from a challenge of *Isospora suis* oocysts. We have isolated a monoclonal antibody which results in the neutralization of sporozoites so that they can not infect ST cells, which is called AM-H7. Furthermore, since sporozoites can infect both ST cells and pigs, and anti-sporozoite antibodies can inhibit the infection of ST cells with sporozoites, it is reasonable to assume that such SN antibodies will inhibit sporozoites in infected pigs.

The present inventors have identified the sporozoite neutralizing proteins, hereinafter referred to as the sporozoite attachment proteins (SAP), using the monoclonal antibody which inhibits the infection of sporozoites in swine testicular cells (Mab-Am-H7) to immunoscreen a cDNA library. The molecular weights of the sporozoite attachment proteins are in the range of 170–220 kDa, as identified by Am-H7 used as a probe for an immunoblot.

In a third aspect, the sporozoite and/or merozoite attachment proteins are used as immunogens in a vaccine. The sporozoite attachment protein was identified by immunoscreening a cDNA library. The merozoite attachment protein may be identified in a similar manner.

These attachment proteins may also be used, in labeled or insolubilized form, as reagents in assays for the presence of *Isospora suis* organisms, or anti-*Isospora* antibodies. They may also be used as immunogens for the production of additional anti-attachment protein antibodies, to be used in any of the ways described previously.

The vaccines of the present invention may be used either to directly immunize piglets, or to immunize sows, whose antibodies will passively protect suckling piglets. Presenting the protective sporozoite and merozoite antigens, including the sporozoite attachment protein, merozoite attachment protein, and/or cell culture derived merozoite antigens, to nursing piglets should result in the active immunization pre-weaned and weaned pigs against challenge from *Isospora suis*. Presenting the protective sporozoite and merozoite antigens, including the sporozoite attachment protein, merozoite attachment protein, and/or cell culture derived merozoite antigens, to pregnant gilts and sows should result in passive protection for the nursing piglets from a challenge of *Isospora suis*.

BRIEF DESCRIPTION OF THE DRAWINGS

FIG. 1 shows the DNA sequence (SEQ ID NO:1) and translated amino acid sequence (SEQ ID NO:2) of the partial cDNA for SAP-1 (clone 411).

FIG. 2 identifies the known amino acid repeat motifs in SAP-1.

DETAILED DESCRIPTION OF THE INVENTION AND ITS PREFERRED EMBODIMENTS

Vaccines

Figure 3A:
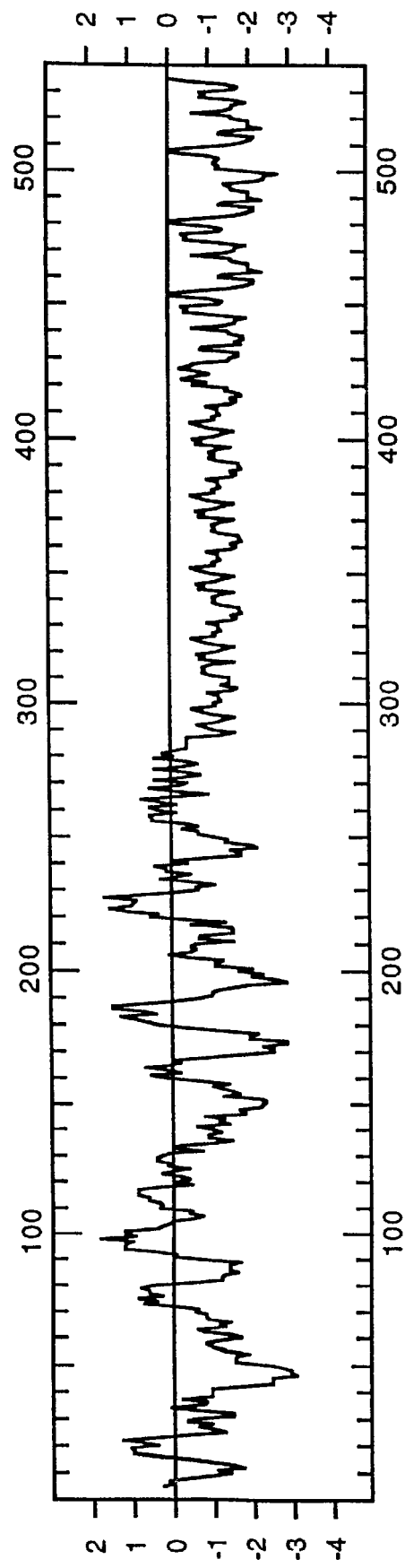
FIGS. 3A–3B show the Kyte-Doolittle hydrophobicity (FIG. 3A) and Hopp-Wood hydrophilicity (FIG. 3B) plots for the SAP-1 AA sequence.

The present invention is directed to vaccines which comprise one or more natural or artificial immunogens presenting one or more epitopes identical to, or functionally equivalent to, epitopes of antigens associated with *Isospora suis* sporozoites, merozoites, or oocysts. In particular, the vaccines of the present invention desirably include (1) a recombinant or isolated sporozoite and/or merozoite attachment protein, and/or (2) one or more merozoite antigens derived from merozoites adapted to cell culture as described herein. The vaccines of the present invention are formulated so that, when administered in one or more doses according to an immunization schedule, the vaccine provides or contributes to protection against one or more strains of *Isospora suis* in pigs.

A vaccine may provide only immunogens against a single pathogen, in which case the vaccine is said to be monovalent, or against two or more different pathogens, in which case the vaccine is said to be polyvalent. Besides providing protection against *Isospora suis*, the vaccine may include other immunogens so that it provides protection against additional porcine pathogens.

A vaccine is a pharmaceutically acceptable composition which comprises one or more immunogens which are capable, when administered to a subject in an effective amount, of eliciting a immune response from the subject which tends to protect that subject from an immunologically related invader, such as a pathogen. Chemically speaking, immunogens of biological origin are most often peptides (including proteins), carbohydrates, glycopeptides, lipids, glycolipids, or lipopeptides.

A vaccine may take the form of a culture, or a concentrate of a culture, of a living pathogen which has been modified ("attenuated") so that it is no longer pathogenic such attenuation may be achieved by, e.g., repeatedly passaging the organism in cell culture. Alternatively, an isolated organism may be inactivated (killed) and then used. Such inactivation may be achieved by physical methods, such as freezing, heat or sonication, and/or by chemical methods, such as treatment with enzymes, thimerosal or acid. Either an attenuated or an inactivated organism will, if used directly in a vaccine, present a variety of immunogens.

A vaccine may alternatively comprise only a subset of the immunogens associated with the whole organism. The inactivated organism may be separated into subcellular components, such as the membrane and the cytoplasm, and these can be used individually in vaccines.

Still another possibility is to formulate a vaccine so that it presents only particular immunogens. These immunogens may be extracted from the cells and/or from the culture medium in which the cells were grown. Such immunogens may be purified to the extent desired, by such processes as chromatography, membrane filtration, centrifugation and extraction. See Asenjo, *Separation Processes in Biotechnology* (1990).

If an immunogen is sufficiently well characterized, it may be duplicated synthetically. For example, a peptide immunogen of known amino acid sequence may either be synthesized by a Merrifield-type sequential coupling of amino acids, or expressed in a host cell transformed with recombinant DNA encoding the desired peptide.

Artificial Immunogens

If the epitopes of an *Isospora suis*-associated antigen are identified, one may present artificial, non-naturally occurring immunogens which incorporate the same or cross-reactive epitopes. An epitope is deemed "associated" with *Isospora* because an antigen bearing the epitope is produced by *Isospora* at any developmental stage. If so, the antigen may be a surface antigen, an intracellular antigen or a "shed" antigen. An epitope may also be deemed associated with *Isospora* if it is borne by a biochemical produced by infected cells of the subject in specific, but non-immunological, response to the disease.

An artificial immunogen may comprise one or more epitopes, which may be the same or different. If the immunogen comprises a plurality of such epitopes, they may be linked directly, or through a spacer of some kind, or by noncovalent means such as an avidin:biotin complex. The immunogen may take any form that is capable of eliciting an immune response. By way of example and not of limitation, the immunogen may be (a) a linear conjugate, head to tail, with or without an intervening linker, of a plurality of epitopes, which is sufficiently large to be immunogenic, (b) a conjugate of one or more epitopes to a soluble immunogenic macromolecular carrier, such as serum albumin, keyhole limpet hemocyanin, or dextran, (c) a recombinant, nonpathogenic virus, bacterium, or fungus engineered to display the epitope on its surface, or (d) a conjugate of a plurality of epitopes to a branched lysine core structure,i.e., a so-called "multiple antigenic peptide" (see Posnett, et al., J. Biol. Chem., 263:1719–25, 1988). The immunogenic conjugate may also comprise moieties intended to enhance the immune response, such as a cytokine or an adjuvant.

An artificial immunogen may comprise B-cell epitopes, T cell epitopes, or both. The epitopes may be ones which occur in nature, although presented, via, the artificial immunogen, in a different number, order, spacing or combination than in any naturally occurring molecule, and/or the epitopes may differ from those which occur in nature.

Preferred embodiments include those in which the antigen comprises one or more copies of the first or second repeats of SAP-1, as defined in FIG. 2, or of a cyclic permutation thereof. It is considered likely that these repeats form epitopes of SAP-1. Preferably, the antigen comprises at least two, preferably at least four, more preferably at least six of either or both of these repeats. The copies may be linked directly, as occurs in SAP-1, or by means of a spacer. This spacer may be one of these which are naturally found to serve as spacers between consensus repeats, or between domains of multiple domain proteins, or it may be an artificial spacer, such as a polyglycine spacer. The number of the first and/or second repeats may exceed the number found natively in SAP-1. The copies may be identical, or all be substantially homologous but not necessarily identical to the consensus repeat sequence. In the case of a substantially homologous sequence, preferably all of the deviations are conservative, more preferably highly conservative, substitutions. The first repeats may precede the second repeats, as in SAP-1, or the reverse, or the first and second repeats may be intercalcated.

It should be noted that the first repeat itself has a fourfold structure, which can be represented as follows:

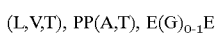

(L,V,T), PP(A,T), E(G)$_{0-1}$E where any one of the set of amino acids within parentheses may appear at that position). This unit may itself be of interest.

The second repeat also has a deeper structure, although one less pronounced than that of the first repeat. Near the beginning of the repeat, note Q(K,R)A(K,R) LPRKES, and, near the end, QQRR(F,Y) LPL(R,K)KS.

Two distinct repeats have been found in a *Cryptosporidium* cell wall protein, see Ranucci, et al., Infection and Immunity, 61:2347–56 (1993) and, especially when the DNA shows synonymous mutations, have been thought to indicate the functional and/or structural importance of the repeats.

Epitope Identification

A B-cell (and antibody) peptide epitope is usually at least five amino acids in length. There is no fixed upper limit on the size of a B-cell epitope, and the epitope can be formed by the folding of the antigen to bring into proximity noncontiguous segments of the molecule.

An T-cell peptide epitope is usually at least five and up to about 24 amino acids long (the longest peptide which can fit in the Class II groove). Of course, the epitope may be presented as a moiety of a larger antigen, which will be processed by the immune system to properly present the T-cell epitope.

Many B-cell and T-cell epitopes are known. Several techniques of identifying additional B-cell and T-cell epitopes are recognized by the art. In general, these involve preparing a molecule which potentially provides a B-cell or T-cell epitope and characterizing the immune recognition of or response to that molecule.

One method of identifying peptide B-cell or T-cell epitopes is by systematic testing of peptide fragments. This can be done in different ways. Thus, one may test a series of peptides which collectively span the entire protein, or at least those regions deemed most likely to present epitopes. The peptides may be equal or unequal in length. One strategy is to divide the protein into, say, two equal fragments, and test each fragment for immunological activity. Each positive fragment is then divided into two subfragments, and the process is repeated until further division yields only negative results. While a divisor of two allows for the most economical search, a larger divisor will reduce the number of separate steps required. The fragments may be overlapping, if desired, to increase the sensitivity of the search. For example, to identify T-cell epitopes, one may prepare a series of twenty-mer peptides with progessive overlap of 5 amino acids, e.g., residues 1–20, 16–35, 31–50, etc., of the original polypeptide. The length of the peptides, and the degree of overlap, is up to the practitioner. The overlap should, however, be at least five amino acids since that is the smallest B-cell or T-cell epitope size. An extreme example of the overlapping peptides strategy is to test a series of peptides of length n, and overlap n-l, where n is typically 5–10. For a protein of size S, S-n+1 peptides are tested. See, e.g., Geysen, U.S. Pat. No. 4,708,871.

Fragments are readily prepared if the amino acid sequence of the peptide is known; a coding sequence may then be constructed for any desired fragment, and the fragment produced by recombinant DNA techniques. If the fragment is small, it may also be prepared by liquid or solid phase peptide synthesis.

If no sequence information is available, a polypeptide antigen may be fragmented with site-specific cleavage agents, such as cyanogen bromide, iodosobenzoic acid, and trypsin. Larger fragments may be obtained by using agents with rarer substrates, or by using the agents in low concentrations, at lower temperatures, or shorter reaction times. Smaller fragments may be obtained by using combinations of agents simultaneously, or by using high concentrations, higher temperatures, or longer reaction times, and optionally using chaotropic agents to help unfold the peptide. The fragments, large or small, are screened. Positive fragments may be fragmented further, by digestion with a different agent, or under more stringent conditions (higher temperature or protease concentration; presence of chaotropic agents to unfold protein, etc.), to localize the epitope.

The number of fragments to be screened may be reduced, if the amino acid sequence is known, by using the amino acid sequence to predict which fragments are likely to act as B-cell or T-cell epitopes. In general, these predictive methods work by assembling a database of known T cell antigenic sites (and perhaps a second database of sequences known not to be B-cell or T-cell epitopes) and comparing these sites with (a) known 3-D structures of the proteins in question, and/or (b) the known amino acid sequence, especially in the vicinity of the site.

While these predictions are not absolutely accurate, they help to focus experimentation upon particular segments of the protein.

The simplest of these predictive tools analyzes sequences for regions of high local hydrophilicity. Each amino acid is given a numerical value representing its hydrophilicity. The values assigned to residues within a "window" corresponding to a region of one or more (usually 5–15) residues within the protein sequence are averaged, and the window is moved and the process repeated. The hydrophilicity scale and window size may be chosen, based on a database of proteins whose epitopes are known, to maximize the prediction success rate. See Hopp and Woods, Proc. Nat. Acad. Sci. USA, 78:3824–28 (1981), who use their own hydrophilicity scale (based on an earlier scale by Levitt), and a hexapeptide window. Another popular scale is that of Kyte and Doolittle, J. Mol. Biol., 157:105–132 (1982).

This analytical approach can be applied to other local measures which correlate well with antigenic determinants, either singly or in combination. Jameson and Wolf, CABIOS, 4:181–86 (1988) constructed an "antigenic index" which weighs hydrophilicity, surface probability, backbone flexibility, and predicted secondary structure.

Margalit, et al., "Prediction of Immunodominant Helper T Cell Antigenic Sites from the Primary Sequence", J. Immunol., 138=2213–29 (1987) has identified (using the AMPHI program), a subset of T cell epitopes which are characterized by the presence of an amphipathic structure. In the Margalit algorithm, the amino acid sequence was converted into sequence of hydrophobicity values (the preferred scale was that of Fauchere-Pliska) and this sequence was divided into overlapping blocks (preferably of length 11). The blocks were examined for periodicity in hydrophobicity consistent with a regular amphipathic helical structure; the preferred power spectrum procedure is a least squares fit of a sinusoid. Margalit preferred to look for a segment of several conservative blocks which has an amphipathic score (the sum of the amphipathic indices of the blocks) of greater than 4.

Other algorithms may be developed by study of the B-cell or T-cell epitope database.

An alternate approach toward characterization of CTL epitopes is to identify them directly. Naturally occurring peptides associated with MHC molecules on the host cells are directly extracted, fractionated by HPLC and used to reconstitute recognition by target specific CTL of a host cell expressing appropriate MHC molecules. Sequencing can be performed by Edman degradation. Mandelboim, et al., Nature, 369:67–71 (1994). Tandem mass spectrometry may be used to evaluate MHC-associated peptides. C. L. Slingluff, et al., J. Immunol. 150:2955 (1993); D. F. Hunt, et al., Science 255:1261 (1992); R. A. Henderson, et al., Proc. Natl. Acad. Sci. USA 90:10275 (1993). An apparatus may be used which allows simultaneous immunological and mass spectrophotometric analysis of the effluent from the HPLC cdumm. Cox, et al., Science, 264:716–18 (1994).

B-cell (antibody) epitopes may be identified by screening in vitro with polyclonal or monoclonal antibodies raised against the organism, or its isolated antigens. Polyclonal antibodies may be obtained from either immunized, or presently or previously infected, animals. Protectivity may be predicted on the basis of whether the epitope is recognized by an antibody which neutralizes sporozoites or merozoites in cell culture or which protects pisgs in vivo. The ultimate test, however, of the vaccinological value of an epitope is to determine whether an immunogen presenting the epitope will immunize an animal against subsequent challenge with the pathogen.

Similarly, the cell-mediated immune response may be assayed in vitro or in vivo. The conventional in vitro assay is a T cell proliferation assay. A blood sample is taken from an individual who suffers from the disease of interest, or from a vaccinated individual. The T cells of this individual should therefore be primed to respond to a new exposure to that antigen by proliferating. Proliferation requires thymidine because of its role in DNA replication. Once a purified T cell population is obtained it is cultured in the presence of irradiated antigen presenting cells (splenic macrophages, B cells, dendritic cells all present). (These cells are irradiated to prevent them from responding and incorporating tritiated thymidine). The viable T cells (100,000–400,000 per well in 100 $\mu$l media supplemented with IL2 at 20 units) are then incubated with test peptides or other antigens for a period of 3 to 7 days with test antigens at concentrations from 1 to 100 $\mu$g/mL.

At the end of the antigen stimulation period a response may be measured in several ways. First the cell free supernatants may be harvested and tested for the presence of specific cytokines. The presence of $\alpha$-interferon, IL2 or IL12 are indicative of a Th helper type 1 population response. The presence of IL4, IL6 and IL10 are together indicative of a T helper type 2 immune response. Thus this method allows for the identification of the helper T cell subset.

A second method termed blastogenesis involves the adding tritiated thymidine to the culture (e.g., 1 $\mu$curie per well) at the end of the antigen stimulation period, and allowing the cells to incorporate the radiolabelled metabolite for 4–16 hours prior to harvesting on a filter for scintillation counting. The level of radioactive thymidine incorporated is a measure of the T cell replication activities. Negative antigens or no antigen control wells are used to calculate the blastogenic response in terms of a stimulation index. This is CPM test/CPM control.

CMI may also be assayed in vivo in a standard experimental animal, e.g., a mouse. The mouse is immunized with a priming antigen. After waiting for the T cells to respond, the mice are challenged by footpad injection of the test antigen. The DTH response (swelling of the test mice is compared with that of control mice injected with, e.g., saline solution. Preferably, the response is at least 0.10 mm, more preferably at least 0.15 mm, still more preferably at least 0.20 mm, most preferably at least 0.30 mm.

When testing a large number of fragments for B or T cell epitope activity, it is possible to use a divide-and-conquer strategy to minimize the number of test animals or cultures required. The fragments may be divided into two or more known groups and all fragments of a group administered to a single animal or culture. If no immune response is observed then all fragments if the mixture is positive, it may then be divided into smaller subgroups and the process repeated.

Functionally Equivalent Epitopes

Once an epitope is identified, functionally equivalent epitopes may be identified by a combination of knowledge of amino acid similarities and systematic variation of the sequence of the epitope.

In addition to epitopes which are identical to the naturally occurring Isospora-specific epitopes, the present invention embraces epitopes which are substantially homologous with such epitopes, and therefore Isospora-specific in their own right.

The term "substantially homologous", when used in connection with amino acid sequences, refers to sequences which are substantially identical to or similar in sequence with each other, giving rise to a homology in conformation and thus to similar (or improved) biological activity. The term is not intended to imply a common evolution of the sequences.

Substantially homologous peptide epitopes may be identified by a variety of techniques. It is known in the art that one may readily synthesize all possible single substitution mutants of a known peptide epitope. Geysen, et al., Proc. Nat. Acad. Sci. (USA), 81:3998–4002 (1984). For a nonpeptide, there are (20×9−1=179) such mutants. While the effects of different substitutions are not always additive, it is reasonable to expect that two favorable or neutral single substitutions at different residue positions in the epitope can safely be combined in most cases.

One class of allowable modifications of the amino acid sequence of a peptide moiety are amino acid substitutions. Conservative substitutions replace an amino acid with another of like size, charge and polarity; these are less likely to substantially alter the conformation of the peptide. The types of substitutions which may be made in the protein or peptide molecule of the present invention may be based on analysis of the frequencies of amino acid changes between a homologous protein of different species, such as those presented in Table 1–2 of Schulz et al., supra and FIGS. 3–9 of Creighton, supra. Based on such an analysis, conservative substitutions are defined herein as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar or slightly polar residues: Met, Leu, Ile, Val (Cys); and
5. Large aromatic residues: Phe, Tyr, Trp. Groups 1–3 are somewhat related and mutations within that set may be considered semi-conservative. Similarly, mutations within groups 4–5 may be considered semi-conservative.

Residues Pro, Gly and Cys are parenthesized because of their special role in protein architecture. Pro imparts rigidity to the peptide chain, and has a tendency to interfere with alpha helix formation. Gly imparts flexibility to the peptide chain, and is often found in "loops" between alpha helices or beta strands. The thiol groups of cysteine residues can be oxidized to form disulfide bonds between nonadjacent cysteinyl residues.

Within the foregoing groups, the following substitutions are considered "highly conservative":

Asp/Glu

His/Arg/Lys

Phe/Tyr/Trp

Met/Leu/Ile/Val

Covalent modifications of amino acids contained in peptides or proteins of interest are included within the scope of the present invention. Such modifications may be introduced into peptides by reacting targeted amino acid residues of the peptide with an organic derivatizing agent that is capable of reacting with selected side chains or terminal residues, or with an enzyme that catalyzes the desired modification, e.g., a glycotransferase to add sugars. The following examples of chemical derivatives are provided by way of illustration and not by way of limitation. Chemical modification (including enzymatic modification) permits the incorporation into the sequence of amino acids which are not genetically encoded.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L- (4-isopropyl)-phenylglycine, D- (trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole-(alkyl)alanines, and D- or L-alkylainines where alkyl may be substituted or unsubstituted methyl, ethyl, propyl, hexyl, butyl, pentyl, iso-propyl, iso-butyl, sec-isotyl, iso-pentyl, non-acidic amino acids, of C1–C20.

Acidic amino acids can be substituted with non-carboxylate amino acids while maintaining a negative charge, and derivatives or analogs thereof, such as the non-limiting examples of (phosphono)-alanine, glycine, leucine, isoleucine, threonine, or serine; or sulfated (e.g., $—SO_3H$) threonine, serine, tyrosine.

Other substitutions may include unnatural hyroxylated amino acids may made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the proteins can be replaced by a ketomethylene moiety, e.g. (—C (=O) $—CH_2—$) for (—(C=O) —NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid representing a component of the said proteins can be replaced by the same amino acid but of the opposite chirality. Thus, any amino acid naturally occurring in the L-configuration (which may also be referred to as the R or S configuration, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of greatly increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of proteins of the present invention may include the following: Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo- beta- (5-imidozoyl) propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl) carbodiimide or 1- ethyl-3-(4-azonia-4,4-dimethylpentyl) carbodiimide. Furthermore, aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithio]propioimidate yield photo-activatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195, 128; 4,247,642; 4,229,537; and 4,330,440 (which are herein incorporated entirely by reference), may be employed for protein immobilization.

Other modifications of proteins of the present invention may include hydroxylation of proline and lysine, phosphorylation of hydroxyl groups of seryl or threonyl residues, methylation of the alpha-amino groups of lysine, arginine, and histidine side chains (T. E. Creighton, Proteins: *Structure and Molecule Properties,* W. H. Freeman & Co., San Francisco, pp. 79–86 (1983)), acetylation of the N-terminal amine, methylation of main chain amide residues (or substitution with N-methyl amino acids) and, in some instances, amidation of the C-terminal carboxyl groups, according to known method steps. Glycosylation is also possible.

Such derivatized moieties may improve the solubility, absorption, permeability across the blood brain barrier biological half life, and the like. Such moieties or modifications of proteins may alternatively eliminate or attenuate any possible undesirable side effect of the protein and the like. Moieties capable of mediating such effects are disclosed, for example, in *Remington's Pharmaceutical Sciences,* 16th ed., Mack Publishing Co., Easton, Pa. (1980).

Such chemical derivatives of proteins also may provide attachment to solid supports, including but not limited to, agarose, cellulose, hollow fibers, or other polymeric carbohydrates such as agarose, cellulose, such as for purification, generation of antibodies or cloning; or to provide altered physical properties, such as resistance to enzymatic degradation or increased antigenic properties, which is desired for therapeutic compositions comprising proteins of the present invention. Such peptide derivatives are well-known in the art, as well as method steps for making such derivatives using carbodiimides active esters of N-hydroxy succinimmide, or mixed anhydrides, as non-limiting examples.

Insertions or deletions of amino acids may also be made. Insertions and deletions are most likely to be tolerated at the amino or carboxy termini, at interdomain segments, at loops, or at other regions of relatively high mobility (e.g., areas which are not well resolved upon X-ray diffraction analysis). However, when the exact effect of the substitution, deletion, or insertion is to be confirmed one skilled in the art will appreciate that the effect of the mutation will be evaluated by routine screening assays. Such screening may be coupled with random mutagenesis so as to simultaneously screen a large number of mutants. It is known that one may randomly mutate one or more residues of an epitope so that any of the twenty possible amino acids, or a selected set (such as all conservative replacements), can occur at that residue position, and screen for mutants with a desired immunological activity. Parmley and Smith, Gene, 73:305–18 (1988); Devlin, et al., Science, 25:49:404–6 (1990); Scott and Smith, Science, 249:386–90 (1990); Greenwood, et al., J. Mol. Biol., 220:821–7 (1991); Cwirla, et al., Proc. Nat. Acad. Sci. (USA), 87:6378–82 (1990); Stephen and Lane, J. Mol. Biol., 225:577–83 (1992); Barrett, et al., Anal. Biochem., 204:357–64 (1992); Ladner, U.S. Pat. No. 5,223, 409.

Such modifications may be made as part of an organic synthesis of a peptide, or by recombinant methods. A recombinant or isolated protein may also be modified, in vitro, by chemical (including enzymatic) means. Recombinant proteins may be mutated by site-specific mutagenesis of the peptide molecule-encoding nucleic acid, expression of the mutant nucleic acid in recombinant cell culture, and, optionally, purification from the cell culture, for example, by immunoaffinity chromatography using a specific antibody on a chemically derivatized column or immobilized membranes or hollow fibers (to absorb the mutant by binding to at least one epitope).

When the primary epitope is a carbohydrate, it may be isolated from nature, or synthesized by suitable glycosylation reactions as known in the art. When the primary epitope is a glycopeptide, the peptide may be synthesized and then glycosylated, either biologically (by expression in a suitable host cell) or chemically.

The foregoing comments apply, mutatis mutandis, to antigens which are not immunogens. Such antigens may be useful as diagnostic reagents.

Pharmaceutical Purposes

The term "protection", as in "protection from infection or disease", as used herein, encompasses "prevention," "suppression" or "treatment." "Prevention" involves administration of a Pharmaceutical composition prior to the induction of the disease. "Suppression" involves administration of the composition prior to the clinical appearance of the disease.

"Treatment" involves administration of the protective composition after the appearance of the disease. It will be understood that in medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "protection," as used herein, is meant to include "prophylaxis." The "protection" provided need not be absolute, i.e., the disease need not be totally prevented or eradicated, provided that there is a statistically significant improvement (p=0.05) relative to a control population. Protection may be limited to mitigating the severity or rapidity of onset of one or more symptoms of the disease.

Pharmaceutical Compositions

The pharmaceutical compositions of the present invention may comprise one or more of the following protective agents:

(a) a protective immunogen;

(b) a vector comprising DNA encoding a protective immunogen which can be expressed in host cells;

(c) an anti-sense nucleic acid which can enter infected cells, or *Isospora* cells, and interfere with expression of an *Isospora* gene;

(d) a protective antibody; or (e) a protective anti-idiotypic antibody.

In addition, it may comprise (f) a drug which interferes with the life processes of one or more stages of *Isospora suis*.

In one embodiment, isolated sporozoite and/or merozoite antigens are used to vaccinate pregnant gilts or sows in order to passively protect nursing piglets from coccidiosis from birth to weaning. A vaccine may be prepared as follows:

(A) Sporozoite and merozoite protective antigens of choice are isolated as described above and frozen at –80° C. until used to prepare a vaccine.

(B) Merozoites are freeze-thawed three times to lyse all of the cells, thus releasing any meronts or merozoites that remain in the swine testicular cells and are pooled with harvested free free swimming merozoites.

(C) The sporozoite and merozoite antigens are packaged or adjuvanted by some process either to protect the antigen for oral application or to provide optimal immunity by parenteral route. For oral applications, this type of coating protects the antigens from denaturation while travelling through the stomach. The antigens could be encapsulated by a mixture of two polymers to form microspheres. The antigens could also be placed inside a protein sphere which dissolves in the small intestine rather than the stomach.

For antigens expressed in bacterial, viral or mammalian (preferably swine testicular cells) expression vectors, the desired plasmid construct is placed into the desired host cells. The bacteria are grown to late exponential phase growth, the desired stabilizer added and the bacteria frozen. The desired host cell includes a cell which is able to attach to the small intestine for a period of time, including such strains as field isolated strains which can colonize the small intestines of pigs but which is not pathogenic to pigs.

Pharmaceutical Administration

At least one antigen of the present invention may be administered by any means that achieve the intended purpose, using a pharmaceutically acceptable composition (vaccine). *Isospora suis* has been found to be extremely stable to heat and chemicals. Due to *I. suis'* extreme stability it is very ubiquitous in nature and all adult pigs have been exposed to this disease. Colostrum and milk of sows and gilts contain antibodies principally associated with 3 immunoglobulin classes; IgA, IgG and IgM. The predominant Ig is dependent upon the method of sensitization. Establishing optimal lactogenic immunity is an important aid in preventing clinical *I. suis* infections in nursing pigs. Several studies demonstrated that when animals are properly sensitized, e.g., by oral exposure, mucosal immunity can subsequently be stimulated by parenteral vaccination. Mucosal immunity can be indirectly measured by evaluating the performance of the lactogenic response. Passive lactogenic immunity correlates with increased neutralizing antibodies of the IgA class of immunoglobulins in colostrum and milk. Traditional means of boosting antibody levels in milk have focused on immunizing the dam prior to parturition. Studies have shown that adult animals do not shed *I. suis* oocysts suggesting life immunity. Due to the stability and ubiquitous nature of *I. suis* all adult pigs have been orally exposed to *I. suis* at one point in their life. Thus we are able to boost the mucosal immunity and consequently optimize the lactogenic immunity by parenterally vaccinating the pregnant animals prior to farrowing providing optimal passive immunity to the nursing piglets.

The administration of such a composition may thus be by various parenteral routes such as subcutaneous, intravenous, intradermal, intramuscular, intraperitoneal, intranasal, transdermal, or buccal routes. Parenteral administration can be by bolus injection or by gradual perfusion over time. The preferred modes of parenterally administering a pharmaceutical composition of the present invention is by subcutaneous, intramuscular or intravenous application.

Alternatively or additionally, the administration may be by an oral route. In this case, the preferred dosage form for sows and young pigs (e.g., 7–21 days of age) is a treated feed, e.g., a crepe feed. Nursing piglets may obtain protective antigens from a milk delivery system, or orally from a syringe. The antigens may be encapsulated in an enteric coating, or microspheres can be used to deliver the antigens to the intestinal tract. Alternative methods of delivery include microspheres or live carriers, such as bacteria such as *E. coli* or *Salmonella*, or a virus such as an adenovirus.

A typical regimen for preventing, suppressing, or treating a disease or condition which can be alleviated by an immune response to the immunogen of the present invention, comprises administration of an effective amount of a pharmaceutical composition as described above, administered as a single treatment, or repeated as enhancing or booster dosages, in accordance with an immunologically effective immunization schedule.

An immunization schedule is a program for the administration of one or more specified doses of one or more specified immunogens, by one or more specified routes of administration, at specified times. The doses may be the same or different, and the interval between doses may vary. If more than one dose is given, the individual doses may be of subimmunogenic amounts, provided that the collective effect of the doses is to protect the subject. The use of 1–3 doses is preferred. However, additional doses may be given. The preferred time interval between doses is 1–3 weeks, but the interval may be smaller or larger if a protective effect is achieved. The individual doses are preferably in the range of $10^5$ to $10^9$ sporozoites or merozoites, or equivalent amounts of isolated or recombinant antigen. Preferably, the schedule protects against a challenge of at least $10^4$ more preferably at least $10^5$, still more preferably at least $10^6$ sporulated oocysts, or equivalent numbers of sporozoites or merozoites.

It is understood that the effective dosage will be dependent upon the age, sex, health, and weight of the recipient, kind of concurrent treatment, if any, frequency of treatment, and the nature of the effect desired. The ranges of effective doses provided below are not intended to limit the invention and represent preferred dose ranges.

The effective dose of a pharmaceutical composition, as described above, is determined through a series of tests which lead to an understanding of what is the minimum effective dose(MED). The MED is defined as that the lowest amount of antigen required to induce a protective response in a animal by a specific vaccination regimen. Several experiments are completed to determine the MED. An example of how one such test is completed is described below. The desired animals are purchased and randomly separated into groups. Each group of animals is vaccinated with given amount of antigen, using a specific vaccination schedule. Therefore, the groups of animals are vaccinated with the range of antigen that is being tested. The vaccinated groups and non-vaccinated control group is challenged with an established procedure which leads to disease in the non-vaccinated control animals. The lowest dose of antigen which leads to protection of the vaccinated animals is defined as the MED. The MED is usually used as a vaccine dose for economic reasons. However, any dose above the MED can be used, up to when the dose becomes toxic in the animals.

Table 1 compiles data from several studies which illustrate the effects of various immunization protocols. This table will assist the skilled worker in determining the MED for an *Isospora suis* vaccine.

Table 2 sets forth nine of the many possible protocols which could be used for *Isospora suis* vaccination of pregnant sows. The time of the vaccinations of the sows suggested below are preferred for our vaccinations. However, the times could be altered, so that 1 to 3 doses could be given at different times, with the last dose still given 1 to 2 weeks prefarrow. In addition, the sexual stages of *Isospora suis,* including oocysts which could be used to isolate sporozoites, can be substituted for either the sporozoite attachment protein or the cell-cultured derived merozoites in Table 2. In addition, any of the described antigens could be packaged in a time released vehicle, so that antigen could be released at different intervals with only one vaccination.

Table 3 similarly describes several vaccination schemes for protection of nursing or weaned pigs. The time of vaccination could be altered so that 1 to 2 doses are given prior to when the pigs are weaned. A time-released vehicle could be also used with these pigs, if desired, to better protect the pigs until they reach to market weight.

The vaccine may include one or more adjuvants known in the literature, such as mineral oils, metabolizable organic oils, emulsifiers or metal salts to enhance the effectiveness of the vaccine. Preferred adjuvants include Freund's incomplete adjuvant and squalene (Shark-oil). It should be understood that while the use of various adjuvant preparations may enhance the effectiveness of this vaccine their use is not necessary to the practice of this method.

As an alternative to a pharmaceutical composition comprising the immunogen of the present invention, per se, the pharmaceutical composition may instead comprise a viral or plasmid vector comprising an expressible gene encoding such an immunogen. The pharmaceutical composition and method would then be chosen so that the vector was delivered to suitable cells of the subject, so that the gene would be expressed and the immunogen produced in such a manner as to elicit an immune response. A preferred vector would be an adenovirus, or a poxvirus such as a Vaccinia virus. In the case of genes encoding naturally occurring proteins, or peptide fragments thereof, one may, but need not, use the DNA sequence which encodes the proteins or peptides in nature. A preferred route for immunization would be scarification.

In the case of genes encoding naturally occurring proteins, or peptide fragments thereof, one may, but need not, use the DNA sequence which encodes the proteins or peptides in nature.

Recombinant vaccinia virus constructs have been used for immunization against hepatitis B (Moss, et al., Nature, 311, 67, 1984), herpes simplex virus (Wacchsman, et al., Biosci. Rep. 8, 323; 334, 1988), parainfluenza type 3 (Spriggs, et al., J. Virol., 62, 1293, 1988), and Lassa fever virus (Fisher-Hoch, et al., Proc. Natl. Acad. Sci. USA, 86, 317, 1989). Vaccinia virus constructs comprising gene for cancer-associated antigens have also been prepared (Lathe, et al., Nature, 326, 878, 1987; Bernards, et al., Proc. Natl. Acad. Sci. USA, 84, 6854, 1987; Estin, et al., Proc. Natl. Acad. Sci. USA, 85, 1052, 1988).

Another possibility is a composition which comprises an anti-idiotypic antibody.

Antibodies

The term "antibody" when used herein without further qualification, is intended to include both "intact" antibody and various fragments which retain antigen binding activity. The antibody may be monoclonal or polyclonal, and may be a hybrid of two antibodies, even of different species. Antibodies may be conjugated to other molecules to produce conjugates useful in diagnosis, therapy, etc. The antibody's variable domain gives the conjugate the ability to bind specifically to particular antigenic targets. The constant domain gives it certain "effector" properties, e.g., complement fixation. The variable domain of one antibody may be combined with the constant domain of another antibody. Moreover, the variable domain may be a hybrid of, e.g., the complementarity determining regions (CDRs) of one antibody and the framework regions of another antibody. The antibody may also be a hybrid of a first antigen binding moiety directed against an antigen and a second moiety directed against a different antigen.

The DNA encoding the heavy and light chains of an antibody of interest may be obtained from a cell (e.g., a hybridoma) which produces that antibody and mutated to conservatively alter the antibody. The pharmaceutical compositions of the present invention include antibody containing compositions.

Mode of Production

The proteins of the present invention may be produced by any conventional technique, including (a) nonbiological synthesis by sequential coupling of component amino acids, (b) production by recombinant DNA techniques in a suitable host cell, and 1(c) isolation from nature The proteins disclosed herein are preferably produced, recombinantly, in a suitable host, such as bacteria from the genera *Bacillus, Escherichia, Salmonella, Erwinia,* and yeasts from the genera *Hansenula, Kluyveromyces, Pichia, Rhinosporidium, Saccharomyces,* and *Schizosaccharomyces,* insect cells, plant cells or mammalian cells (such as monkey CV1, COS and CV1 cells, murine C127 and 3T3 fibroblasts, primate cells, and Chinese hamster ovary (CHO) cells. The more preferred hosts are microorganisms of the species *Pichia pastoris, Bacillus subtilis, Bacillus brevis, Saccharomyces cerevisiae, Escherichia coli* and *Yarrowia lipolytica.*

The gene used to encode the protein may be the native DNA sequence, or a modified sequence. Reasons for modification include introduction or elimination of restriction sites to facilitate later manipulation, replacement of native codons with codons preferred by the desired host cell, elimination of possible secondary structures in the corresponding mRNA that might interfere with expression, reduction of the likelihood of a recombination event which would interfere with expression, and modification of the corresponding amino acid sequence. The DNA may be a cDNA, a genomic DNA, a synthetic DNA, or a combination thereof.

Any promoter, regulatable or constitutive, which is functional in the host may be used to control gene expression. To achieve non-transient expression, there are but two requirements:

(a) the coding sequence must be operably linked to a control sequence to form a gene which is functional in the host cell, and (b) the gene must be replicated in the host cell.

Considering criterion (a) first, it is likely that for any host cell of interest, one or more genes have been cloned, or can be cloned, without undue experimentation. The coding sequence may then be linked to this endogenous control sequence in the same manner as the endogenous coding sequence had been linked. A second, but related approach, is to use the control sequence of a gene of a virus which infects the host cell of interest. If for some reason, neither of these approaches is convenient, it was within ordinary skill to use a promoter from a gene of another species of host cell, preferably one which is taxonomically related to the host cell of interest. It is well known that promoters can have cross-species activity; the mouse metallothionein-I promoter, for example, has been used to control expression is fish cells. Another example of promoter use across species (a murine promoter used to express a gene in chicken cells, is given in Chepelinsky AB, King DR, Zelenka PS, and Piatigorsky J. Lens-specific expression of the CAT gene promoted by 5' flanking sequences of the murine alpha A-crystallin gene in explanted chicken lens epithelia. Proc. Nat. Acad. Sci., 82:2334 (1985).

With regard to criterion (b), the replication may be either autonomous, or chromosomal. For autonomous replication, the recombinant DNA molecule must carry, besides the gene, an origin of replication which is functional in the host cell. Plasmids, which replicate autonomously, are found widely in nature. Although some have a narrow host range, others have a broad bacterial host range (see Franklin FCH., Broad host range cloning vectors for gram negative bacter, in "DNA cloning", vol. 1, pp. 165–184, edited by D. M. Glover, published by IRL Press, 1985).

Alternatively, the gene may be cloned into a virus which infects the cell, and which then either replicates autonomously, or integrates into the host cell genome. Again, many viruses have a broad host range. Although some viruses such as bovine papilloma, which have been used to overproduce specific proteins, have a limited host range (see Pavlaxis GN, Felber BK, Wright CM, Papamatheakis J. and Tse T., Applications of bovine papilloma viral and retroviral vectors, in "Gene transfer vectors for mammalian cells", pp. 29–38, edited by J. H. Miller and M. P. Calos, published by Cold Spring Harbor Laboratory, 1987), other viruses, such as Vaccinia, have a broad host range capable of infecting a variety of animals and replicating in a variety of tissue culture cells (see Piccinni A, Perkus ME, and Paoletti E., Vaccinia virus as an expression vector, in "Methods in Enzymology", vol. 153, pp. 545–563, edited by R. Wu and L. Grossman, published by Academic Press, 1987;Moss B., Vaccinia virus expression vectors, in "Gene transfer vectors for mammalian cells", pp. 10–14, edited by J. H. Miller and M. P. Calos, published by Cold Spring Harbor Laboratory, 1987). For other viruses, such as the murine retroviruses, which normally have a fairly broad host range (see Sorge J., Wright D, Erdman VD, and Cutting AE., Ampotropic retrovirus vector system for human cell gene transfer, Mol. Cell. Biol. 4:1730, 1984) the host range may by modified or further extended by altering the protein coat into which the viral vector is packaged (see Clone RD, and Mulligan RC, High-efficiency gene transfer into mammalian cells; Generation of helper-free recombinant retrovirus with broad mammalian host range, Proc. Nat. Acad. Sci. 81:6349, 1984).

Further guidance as to the techniques for achieving expression in a variety of host cells is given by the following publications:

Bacteria Other Than *E. Coli*

Dubnau D. Molecular cloning in Bacillus subtilis, in "Experimental Manipulation of Gene Expression", pp. 33–53, edited by M. Inouye, published by Academic Press, 1983.

Yeast

Broach JR, Li YY, Wu LC, and Jayaram M. Vectors for High-Level, Inducible Expression for Cloned Genes in Yeast, in "Experimental Manipulation of Gene Expression", pp. 84–118, edited by M. Inouye, published by Academic Press, 1983.

Ritter GA, Egan KM, Kiski RA, Jones MO, Elliott SG, and Giffin JC, Expression and Secretion Vectors for Yeast, in "Methods in Enzymology", vol. 153, pp. 516–544, edited by R. Wu and L. Grossman, published by Academic Press, 1987.

Hopwood DA, Bibb MJ, Chater KF, and Kieser T., Plasmid and phage vectors for gene cloning and analysis in Streptomyces, in "methods in Enzymology" vol. 153. pp. 116–165, edited by R. Wu and L. Grossman, published by Academic Press, 1987.

Insects

Summers, M. D. and Smith, G. E. 1987. A manual of methods for baculovirus vectors and insect cell culture procedures. Texas Agricultural Experiment Station Bulletin No. 155. College Station, Tex.

Jeang, K., Giam, C., Nerenberg, M., and Khoury, G., 1987. Abundant synthesis of functional T-cell leukemia virus type I p40x protein in eucaryotic cell by using a baculovirus expression vector. J. Virol. 61:708–713.

Matsuura, Y., Possee, R. D., and Bishop, D. H. L., 1987. Baculovirus expression vectors: The requirements for high level expression of proteins, including glycoproteins., J. Gen. Virol. 68:1233–1250.

Luckow, V. A. and Summers, M. D., 1988. Trends in the development of baculovirus expression vectors. Bio/Technology 6:47–55.

Maiorella, B., Inlow, D., Shauger, A., and Harano, D., 1988. Large-scale insect cell culture for recombinant protein production. Bio/Technology 6:1406–1410.

Miller, L. K., 1988. Baculoviruses as gene expression vectors. Annu. Rev. Microbiol. 42:177–199.

Miller, D. W., Safer, P., and Miller, L. K., 1986. An insect baculovirus host vector for high-level expression for foreign genes. In Genetic Eng., vol 8 (J. K. Setlow and A. Mollaender, eds.), pp. 277–298. Plenum, New York.

Plants

Rogers SG, Klee HJ, Horsch RB, and Fraley RT. Improved vectors for plant transformation: expression cassette vectors and new selectable markers, in "Methods in Enzymology" vol. 153, pp. 253–275, edited by R. Wu and L. Grossman, published by Academic Press, 1987.

Deblaere r., Reynaerts A., Hofte H., Hernalsteens JP, Leemans J., and Van Montagu M. Vectors in cloning in plant cells, in "Methods in Enzymology", vol. 153, pp. 277–291, edited by R. Wu and L. Grossman, published by Academic Press, 1987.

Preferred bacterial promoters include bacteriophage promoters such as the lambda $P_L$ and T7 gene 10 promoters, native bacterial promoters such as the trp promoter, and hybrid promoters such as the Tac (trp/lac) promoter.

Preferred yeast promoters include constitutive promoters such as GAP, PGK (phosphoglycerate kinase) and alpha-factor promoters, and regulatable promoters such as the yeast metallothionein, Gal1–10, GAL7, ADHI and PH05 promoters. Various hybrid promoters are known.

Preferred insect cell promoters include the baculovirus polyhedrin promoter.

Preferred mammalian cell promoters include the metallothionein, heat shock, and cytomegalovirus promoters.

Other regulatory sequences, such as terminators and enhancers, may also be employed.

Preferably, the expression system used is one which places a small peptide on the end of the recombinant protein, which is used as a binding site in the affinity purification of the protein, in one step, from an extract. Such systems include the Kodak International Biotechnologies Flag Epitope System and the GST Gene Fusion System vectors from Pharmacia LKB Biotechnology. (Similar systems are available from other vendors.)

The Flag Epitope System incorporates an octapeptide called M2 at the C-terminus or N-terminus end of a protein. This reported sequence can be used for purifying proteins with an anti- Flag M2 affinity gel or as an antigen in an ELISA assay. A vector uses the omp A signal peptide to express proteins in the periplasmic space of *E. coli*.

Subcloning to the Flag vector system is very simple. The double-stranded cDNA made for the cDNA library contains an EcoRI site on the 5' end of the cDNA with an XhoI site on the 3' end. The multiple cloning site in vectors pFlag-1 and pFlag-2 contain both of these restriction sites in the correct orientation. The cDNA of interest is isolated by digestion with EcoRI and XhoI. The vectors of choice are cut with EcoRI and XhoI, and the insert ligated into the vector in the correct orientation. These two vectors express proteins with the M2 on the 5' end of the recombinant protein for periplasmic and cytoplasmic expression, respectively.

The expressed proteins are isolated from the host cell using the anti-Flag M2 affinity gel chromatography. The purified recombinant proteins are used to produce hyperimmune serum in laboratory animals. The serum is then evaluated by SN assay to determine if it contains neutralizing antibodies. The recombinant proteins are placed into an antigen group based on the ability to react with antibodies to the native protein of interest.

The isolated cDNA that cannot be expressed in the *E. coli* is expressed in *S. cerevisiaie*, Baculovirus and/or swine testicular cell cultures. These expression systems produce the recombinant proteins in a conformation that produces the correct immunological response. The recombinant proteins are purified using the anti- Flag M2 affinity gel chromatography.

Standard reference works setting forth the general principles of recombinant DNA technology include Watson, J. D. et al., *Molecular Biology of the Gene*, Volumes I and II, The Benjamin/Cummings Publishing Company, Inc., publisher, Menlo Park, Calif. (1987); Darnell, J. E. et al., *Molecular Cell Biology*, Scientific American Books, Inc., publisher, New York, N.Y. (1986); Lewin, B. M., Genes III, John Wiley & Sons, publishers, New York, N.Y. (1989); Old, R. W., et al., *Principles of Gene Manipulation: An Introduction to Genetic Engineering*, 2d edition, University of California Press, publisher, Berkeley, Calif. (1981); Ausubel et al, eds., *Current Protocols in Molecular Biology*, Wiley Interscience, publisher, New York, N.Y. (1987, 1992); and Sambrook et al., *Molecular Cloning: A Laboratory Manual*, Second Edition, Cold Spring Harbor Laboratory, publisher, Cold Spring Harbor, N.Y. (1989), the entire contents of which references are herein incorporated by reference.

Chemical Peptide Synthesis

Chemical peptide synthesis is a rapidly evolving area in the art, and methods of solid phase peptide synthesis are well-described in the following references, hereby entirely incorporated by reference: (Merrifield, B., *J. Amer. Chem. Soc.* 85:2149–2154 (1963); Merrifield, B., *Science* 232:341–347 (1986); Wade, J. D., et al., *Biopolymers* 25:S21-S37 (1986); Fields, G. B., *Int. J. Polypeptide Prot. Res.* 35:161 (1990); MilliGen Report Nos. 2 and 2a, Millipore Corporation, Bedford, Mass., 1987) Ausubel, et al, supra, and Sambrook, et al, supra.

In general, as is known in the art, such methods involve blocking or protecting reactive functional groups, such as free amino, carboxyl and thio groups. After polypeptide bond formation, the protective groups are removed (or de-protect-ed). Thus, the addition of each amino acid residue requires several reaction steps for protecting and deprotecting. Current methods utilize solid phase synthesis, wherein the C-terminal amino acid is covalently linked to an insoluble resin particle large enough to be separated from the fluid phase by filtration. Thus, reactants are removed by washing the resin particles with appropriate solvents using an automated programmed machine. The completed polypeptide chain is cleaved from the resin by a reaction which does not affect polypeptide bonds.

In the more classical method, known as the "tBoc method," the amino group of the amino acid being added to the resin-bound C-terminal amino acid is blocked with tert-butyloxycarbonyl chloride (tboc). This protected amino acid is reacted with the bound amino acid in the presence of the condensing agent dicyclohexylcarbodiimide, allowing its carboxyl group to form a polypeptide bond the free amino group of the bound amino acid. The amino-blocking group is then removed by acidification with trifluoroacetic acid (TFA); it subsequently decomposes into gaseous carbon dioxide and isobutylene. These steps are repeated cyclically for each additional amino acid residue. A more vigorous treatment with hydrogen fluoride (HF) or trifluoromethanesulfonyl derivatives is common at the end of the synthesis to cleave the benzyl-derived side chain protecting groups and the polypeptide-resin bond.

More recently, the preferred "Fmoc" technique has been introduced as an alternative synthetic approach, offering milder reaction conditions, simpler activation procedures and compatibility with continuous flow techniques. This method was used, e.g., to prepare the peptide sequences disclosed in the present application. Here, the ∝-amino group is protected by the base labile 9-fluorenylmethoxycarbonyl (Fmoc) group. The benzyl side chain protecting groups are replaced by the more acid labile t-butyl derivatives. Repetitive acid treatments are replaced by deprotection with mild base solutions, e.g., 20% piperidine in dimethyl-formamide (DMF), and the final HF cleavage treatment is eliminated. A TFA solution is used instead to cleave side chain protecting groups and the peptide resin linkage simultaneously.

At least three different peptide-resin linkage agents can be used: substituted benzyl alcohol derivatives that can be cleaved with 95% TFA to produce a peptide acid, methanolic ammonia to produce a peptide amide, or 1% TFA to produce a protected peptide which can then be used in fragment condensation procedures, as described by Atherton, E., et al., *J. Chem. Soc. Perkin Trans.* 1:538–546 (1981) and Sheppard, R. C., et al., *Int. J. Polypeptide Prot. Res.* 20:451–454 (1982). Furthermore, highly reactive Fmoc amino acids are available as pentafluorophenyl esters or dihydro-oxobenzotriazine esters derivatives, saving the step of activation used in the tBoc method.

Transgenic and Chimeric Pigs

Alternatively, pigs may be protected by introducing a gene encoding a protective immunogen or antibody into suitable cells of the pig if only somatic cells are affected, the pig is considered "chimeric". If germ cells are affected (so that the gene is transmissible to offspring), the pig is transgenic.

Linearized DNA bearing the gene may be introduced into a gamete, or microinjected into the pronuclei of fertilized eggs, into the cytoplasm, into the nuclei of two-cell embryos, into individual cells of a blastocyst, or into the blastocoel cavity. (Some of these targets may be reached by electroporation instead of microinjection.) Alternatively, a retrovirus bearing the gene may be constructed and used to infect preimplantation embryos or tissue culture cells (e.g., embryonic stem cells) which may be aggregated with such embryos. In either case, the genetically modified zygote, after a brief in vitro cultivation, is implanted into a foster mother and carried to term. Retroviruses may also be used to deliver genes to fetuses and to postnatal animals. For "gene therapy" post partum, see Cline, et al., Nature, 284:422–425 (1980); Williamson, Nature 298:416–18 (1982).

Again, the gene is operably linked to a promoter functional in the host, and the promoter may be constitutive or regulatable. Preferably, expression is regulated so abnormal embryonic or fetal development is avoided.

Cell Culture

Heretofore, *Isospora suis* has not been successfully grown in mammalian cells or ST cells beyond the early asexual stages. The cell culture derived *Isospora suis* antigens provide a distinct advantage over the isolation of this organism from pigs, due to the costs associated with using pigs and the many pathogens which are present in the swine population. Analysis of the *Isospora suis* asexual and sexual stages produced in ST cells by electron microscopy have demonstrated that the cell culture derived *Isospora suis* stages are very similar to what is observed in the stages isolated from the pig. This fact, with the data presented below that cell culture derived merozoites are able to infect the pig and produce nonviable (but antigenic) oocysts, demonstrates the usefulness of the cell culture derived antigens.

For practice of the present invention, any materials and methods equivalent to those described herein can be used, but the more preferred choices are presented hereunder.

Cell culture derived merozoites, and sexual stages of *Isospora suis* can be produced using basic cell culture technology, as described below. *Isospora suis* sporozoites (frozen or freshly released from oocysts) are used to inoculate ST cells. ST cells are a diploid cell line whose purity from contamination (bacterial, mycoplasma, and extraneous viruses) and chromosomal stability (no chromosomal anomalies) has been determined according to government guidelines, and are registered for vaccine production by the USDA. ST cells can be obtained from American Type Cell Culture, by request, using number CRL 1746.

The medium used for growth of ST cells may comprise any basal medium and supplement which will support growth of the ST cells and asexual-sexual stages of *Isospora suis*, such as Dulbecco's minimal essential medium (DMEM)+10% bovine serum (This type of media is designated parasite propagation media or PPM for short.). ST cell cultures can be grown in microtiter plates, tissue culture tubes, leighton slides, 32 oz bottles, and various size roller bottles that are plastic or glass, and/or continuous culture devices, such as a bioreactor. The cells become confluent several days after planting usually within 4 to 7 days.

The cell culture derived asexual and sexual stages of *Isospora suis* can be produced by the inoculation of the ST cells with sporozoites. Any procedure which leads to the release of sporozoites from the oocysts could be used. The preferred procedure we used to isolate sporozoites is completed in a two step process, as previously described by Lindsay(Lindsay, et al, 1983, Excystation of *Isospora suis* Biester, 1934 of Swine, Z Parasitenkd 69:27–34) with some slight modifications. The sporulated oocysts were purified from contaminating feces and debris by suspending the sporulated oocysts in Sheathers sugar solution and then centrifuging at 1,900×g for 20 minutes. The oocysts were collected on the surface, resuspended in PBS, pH 7.4 and washed three times by centrifugation, 1,900×g for 20 minutes. After purification and washing the oocysts are resuspended in a small volume of PBS (2–5 ml). The outer three layers of the oocysts were removed by using a Wheaton tissue grinder with a teflon pestle. The sporozoites were removed from the sporocysts, the inside membrane that covers the sporozoites, by incubating them at 37° C. with gentle agitation in 0.75% bile-0.25% trypsin until the majority sporozoites were released. The sporozoites were washed three times with the desired buffer to remove the bile and trypsin. No trypsin bile is used for the sporozoites that are stored frozen. They are quickly thawed and washed three times in PBS as described above and are then ready for inoculation.

The *Isospora suis* sporozoites are used to inoculate the ST cells at a multiplicity of infection between 0.0001 to 0.5 sporozoites to ST cells. Multiplicity of Infection(MOI) is defined as the ratio of sporozoites to cells. The sporozoites are suspended in any basal media with or without serum which could be used to maintain the ST cells and life cycle of *Isospora suis* in the ST cells. The preferred inoculation media is a basal media with no serum. The ST cells are rinsed 3 times with basal medium and the sporozoites are added in a small volume which will just cover the ST cells. The sporozoites are incubated with the ST cells for 15 to 120 minutes, with the preferred time of 75 min. The inoculum is rinsed preferably 3 times with basal media with or without serum. The preferred media used to propagate merozoites contains a basal media(e.g., DMEM) plus 1 to 15% bovine calf serum, preferred concentration being 10%, or any other supplement which will support growth of ST cells(i.e. Excel 320, manufactured by JRH). Serum replacements conventionally used in serum-free media, typically including proteins such as transferrin and albumin, may be substituted for serum. The preferred PPM is DMEM+10% serum, which is made by using 900 ml sterile tissue culture grade water, 100 ml 1X filter sterilized DMEM(+L-glutamine), 20 mM HEPES, 0.36% sodium bicarbonate, 200 mg/mL gentamycin, filter sterilized; pH 7.2–7.4. Rolling, stationary, and continuous cultures can be used to produce desired stages of this parasite. Merozoites can also be grown in a $CO_2$ incubator.

Initial experiments were conducted without serum. Cultures were then not able to last longer then 7 to 9 days past the inoculation with sporozoites, in part due to the destruction of the ST monolayer during the growth of the merozoites. The addition of serum resulted in the successful growth of the asexual and sexual stages of *I. suis,* for all or some of the following reasons: 1.) Serum allows for the continued growth of the ST cells, 2.) Serum nonspecifically binds the toxins or enzymes released from the cells as the merozoites spread cell to cell, 3.) Serum adds required nutrients for *I. suis* propagation. The following observations were made following the inoculation of ST cells with sporozoites as a preferred MOI of 0.0025(If a higher MOI is used like, 0.1 to 0.3, the entire ST cell layer is destroyed in 4 to 6 days, even with serum).

The following observations were made regarding the development of *Isospora suis* in cultures.

1. A majority of the sporozoites enter the ST cells in the first 40 minutes. The sporozoite is observed to turn in a clockwise manner to enter the cell, and requires about 10 minutes to invade the ST cell.
2. The sporozoites which have invaded an ST cell remain easily seen by microscopic examination for several hours, but become difficult to find in the ST cells for the next 24 h.
3. The meronts are observed to divide 24 to 48 h post-infection(PI). The first signs of cytopathic effect(CPE) are observed 2 to 3 days PI. CPE has been observed to be due to the exit of the merozoites from the infected cell. The exiting merozoites are free-swimming for a short period of time, until they invade neighboring ST cells.
4. The asexual stages of this parasite are seen from the time of infection to 12–14 days PI or when the culture dies.
5. The sexual stages are first seen around the seventh day PI to 12–14 days PI. Oocysts are seen as early as 7 days PI, with many seen after 10 days PI. This sequence of events corresponds with the life cycle as described in pigs.

The following three methods may be used to isolate the merozoites with the first method being the method of preference. The invention is not limited to these three methods.

1. The asexual and sexual stages of the *Isospora suis* is preferably harvested periodically from the culture by removing the PPM, and pelleting the *Isospora suis* cells by centrifugation at 550×G for 15 min. Harvest of merozoites has approached 125 times the number of sporozoites used to originally inoculate the ST cells. This number can be increased by several methods, including using a lower MOI, adding ST cells to existing *Isospora suis,* and adding the necessary nutrients to the culture periodically. For nonswimming or intracellular merozoites one of the following two methods is preferred.
2. Infected cells can be lysed by freezing and thawing the infected cells 1 to 3x.
3. The infected cells can by lysed by treating with trypsin-bile as described above.

Other agents that can be used but are not preferred would be:

other sources of bile like 0.5% taurodeoxycholic acid (active ingredient of bile). See Xie, et al. Parasitol. Res., 76:566–9 (1990). Our source of bile comes from cattle; other animal species sources could be used as well.

other proteolytic enzymes like pancreatin, chymotrypsin, alpha trypsin but crude trypsin as we use is preferred. -Any other means of mechanical release other then the tissue homogenizer we specified.

In Vitro Diagnostic Methods and Reagents

The proteins of the present invention, and antibodies which specifically bind them, may be used as reagents in a qualitative or quantitative assay, e.g., for the sporozoite or merozoite attachment protein. In order to detect the presence, or measure the amount, of an analyte, the assay must provide for a signal producing system (SPS) in which there is a detectable difference in the signal produced, depending on whether the analyte is present or absent (or, in a quantitative assay, on the amount of the analyte). The detectable signal may be one which is visually detectable, or one detectable only with instruments. Possible signals include production of colored or luminescent products, alteration of the characteristics (including amplitude or polarization) of absorption or emission of radiation by an assay component or product, and precipitation or agglutination of a component or product. The term "signal" is intended to include the discontinuance of an existing signal, or a change in the rate of change of an observable parameter, rather than a change in its absolute value. The signal may be monitored manually or automatically.

The component of the signal producing system which is most intimately associated with the diagnostic reagent is called the "label". A label may be, e.g., a radioisotope, a fluorophore, an enzyme, a co-enzyme, an enzyme substrate, an electron-dense compound, an agglutinable particle.

The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, $^{14}C$, and, preferably, $^{125}I$.

It is also possible to label a compound with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

Alternatively, fluorescence-emitting metals such as $^{125}Eu$, or others of the lanthanide series, may be attached to the reagent using such metal chelating groups as diethylenetriaminepentaacetic acid (DTPA) of ethylenediaminetetraacetic acid (EDTA).

The reagent also can be detectably labeled by coupling to a chemiluminescent compound. The presence of the chemiluminescently labeled reagent is then determined by detecting the presence of luminescence that arises during the course of a chemical reaction. Examples of particularly useful chemiluminescent labeling compounds are luminol, isolumino, theromatic acridinium ester, imidazole, acridinium salt and oxalate ester.

Likewise, a bioluminescent compound may be used to label the reagent. Bioluminescence is a type of chemiluminescence found in biological systems in which a catalytic protein increases the efficiency of the chemiluminescent reaction. Important bioluminescent compounds for purposes of labeling are luciferin, luciferase and aequorin.

Enzyme labels, such as horseradish peroxidase and alkaline phosphatase, are preferred. When an enzyme label is used, the signal producing system must also include a substrate for the enzyme. If the enzymatic reaction product is not itself detectable, the SPS will include one or more additional reactants so that a detectable product appears.

Assays may be divided into two basic types, heterogeneous and homogeneous. In heterogeneous assays, the interaction between the affinity molecule and the analyte does not affect the label, hence, to determine the amount or presence of analyte, bound label must be separated from free label. In homogeneous assays, the interaction does affect the activity of the label, and therefore analyte levels can be deduced without the need for a separation step. In one embodiment, the reagent is insolubilized by coupling the affinity molecule to a macromolecular support, and analyte in the sample is allowed to compete with a known quantity of a labeled or specifically labelable analogue. The "analogue" is a molecule capable of competing with the analyte for binding to the affinity molecule, and the term is intended to include native analyte itself. It may be labeled already, or it may be labeled subsequently by specifically binding the label to a moiety differentiating the analogue from the analyte. The solid and liquid phases are separated, and the labeled analogue in one phase is quantified. The higher the level of analogue in the solid phase, i.e., sticking to the affinity molecule, the lower the level of analyte in the sample.

In a "sandwich assay", both an insolubilized binding protein, and a labeled binding protein are employed. The analyte is captured by the insolubilized affinity molecule and is tagged by the labeled affinity molecule, forming a tertiary complex. The reagents may be added to the sample in either order, or simultaneously. The affinity molecules may be the same or different. The amount of labeled affinity molecule in the tertiary complex is directly proportional to the amount of analyte in the sample.

The two embodiments described above are both heterogeneous assays. However, homogeneous assays are conceivable. The key is that the label be affected by whether or not the complex is formed.

A label may be conjugated, directly or indirectly (e.g., through a labeled anti- antibody), covalently (e.g., with SPDP) or noncovalently, to the affinity molecule, or analyte analogue, to produce a diagnostic reagent. Similarly, the affinity molecule or analyte analogue may be conjugated to a solid-phase support to form a solid phase ("capture") diagnostic reagent. Suitable supports include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to its target. Thus the support configuration may be spherical, as in a bead, or cylindrical, as in the inside surface of a test tube, or the external surface of a rod. Alternatively, the surface may be flat such as a sheet, test strip, etc.

Non-Medical Uses

Proteins, in general, can be used as molecular weight markers for reference in the separation or purification of proteins by electrophoresis or chromatography. In many instances, proteins may need to be denatured to serve as molecular weight markers. A second general utility for proteins is the use of hydrolyzed protein as a nutrient source. Hydrolyzed protein is commonly used as a growth media component for culturing microorganisms, as well as a food ingredient for human consumption. Enzymatic or acid hydrolysis is normally carried out either to completion, resulting in free amino acids, or partially, to generate both peptides and amino acids. However, unlike acid hydrolysis, enzymatic hydrolysis (proteolysis) does not remove non-amino acid functional groups that may be present. Proteins may also be used to increase the viscosity of a solution.

The proteins of the present invention may be used for any of the foregoing purposes, as well as for therapeutic and diagnostic purposes as discussed further earlier in this specification.

EXAMPLES

Generation of Cell Culture Derived Merozoites for Vaccine use In Pregnant Gilts

Sporulated oocysts were purified from contaminating feces and debris by suspending the sporulated oocysts in Sheathers sugar solution and then centrifuging at 1,900×g for 20 minutes. The oocysts were collected on the surface, resuspended in PBS, pH 7.4 and washed three times by centrifugation, 3,080×g for 20 minutes. After purification and washing the oocysts were resuspended in a small volume of PBS (2–5 ml ). The outer three layers of the oocysts were removed by using a Wheaton tissue grinder with a teflon pestle. The sporozoites were removed from the sporocyst, the inside membrane that covers the sporozoites, by incubating them at 37° C. with gentle agitation in 0.75% bile-0.25% trypsin until the majority sporozoites were released. The sporozoites were centrifuged at 1900×g for 15 minutes. The pellet was resuspended in Eagles MEM(no serum). A 20 ml suspension of sporozoites representing an MOI of 0.03 to 0.3 was used to inoculate several confluent ST cell culture roller bottles. The roller bottles were returned to the rolling apparatus and incubated for 60 to 90 minutes at 37° C. The inoculum was rinsed off three times and fresh basal medium as described above was added to each bottle (no serum). Free swiming merozoites were periodically harvested from the infected cultures by removing the media from the inoculated cells and replenishing with fresh basal medium. The harvested fluids were centrifuged at 550×g for 15 to 30 minutes. The pellets were suspended in a small volume of basal medium plus 1% glucose and were stored at −70° C. until use. Furthermore as cell cultures began to develop cytopathic effects infected cell layer was harvested by removing the culture fluids and adding 10 to 20 ml of the trypsin-bile solution described above. The bottles were returned to the incubator for 15 to 30 minutes when all the ST-cells were microscopically observed to be lysed. This harvest was centrifuged and stored as described above.

Infectivity of Sporozoites

To assess the infectivity of the isolated sporozoites, colostrum deprived, Cesarean derived pigs were divided into the following groups:

Group 1, two CDCD pigs which were challenged orally via a syringe with an optimum level of oocysts to produce clinical disease ($6.25 \times 10^3$ oocysts);

Group 2, two CDCD pigs were challenged with $2 \times 10^5$ sporozoites orally. The sporozoites were purified on 25% sucrose to remove any oocysts;

Group 3, two CDCD pigs were challenged with $2 \times 10^5$ sporozoites orally, approximately five minutes following the administration of 0.1 g sodium bicarbonate resuspended in 2 ml phosphate buffered saline.

Both pigs in Group 1 shed oocysts 6, 7, and 8 days post challenge. Both pigs had clinical signs of infection seven to thirteen days post challenge.

One pig in Group 2 shed oocysts seven to thirteen days post challenge. One pig shed oocysts seven to twelve days post challenge. One pig had no clinical signs of infection, and one pig had clinical evidence of infection twelve to thirteen days post challenge.

Both pigs in Group 3 shed oocysts seven to ten days post challenge. Both pigs had clinical signs days 9–13 post challenge.

The above demonstrated that sporozoites alone are infectious to pigs. It was then demonstrated that sporozoites are infectious when given orally to conventional SPF pigs. Twelve two day old pigs were purchased from a specific pathogen free herd and were separated randomly into three groups of pigs, each group containing four pigs and housed in separate isolation areas. Group 1 was a control group which received $1.2 \times 10^4$ oocysts orally. Groups 2 and 3 received $8 \times 10^5$ sporozoites orally, and pigs in Group 3 received 0.1 g sodium bicarbonate five minutes prior to the sporozoites. Oocysts were observed in the feces from all of the pigs. Ten of the twelve pigs had clinical signs of infection. One pig in Groups 1 and 3 did not have clinical signs of infection. Thus, the sporozoites were found to be infectious when given orally to conventional pigs.

Method of Freezing Sporozoites

A method was developed for freezing sporozoites so that they remain infectious for swine testicular cells and for pigs. Ten plastic vials containing $1 \times 10^6$ sporozoites in 1 ml 5% dimethylsulfoxide (DMSO), a cryoprotectant, and 10 vials in 10% DMSO, were frozen at −150° C.

The frozen sporozoites were first tested by infection of swine testicular cells. It was found that sporozoites frozen for 52 weeks at −150° C. are infectious in swine testicular cells.

When five day old pigs were inoculated with animal-derived sporozoites frozen for six weeks at −150° C., the pigs exhibited disease. Pigs were divided into three groups as follows: Group 1 received $1 \times 10^5$ frozen sporozoites; Group 2 received $4 \times 10^5$ frozen sporozoites; Group 3 received $1.25 \times 10^4$ oocysts. All of the pigs were observed to shed oocysts in their feces. It was thus established that sporozoites frozen for six weeks at −150° C. are infectious and able to reproduce disease in five day old pigs.

Isolation of Merozoites from Pigs

Both type I and type II merozoites were isolated by the same method. Four pigs were challenged with as many oocysts as possible while still remaining alive up to six days post-challenge. The number of oocysts used for this challenge ranged from $1 \times 10^5$ to $5 \times 10^5$ oocysts per pig. Pigs with the most severe clinical signs were sacrificed on day five or six post-challenge. The small intestines were removed from the pigs and a longitudinal cut was made throughout the length of the intestine. The intestinal content was discarded and the tissue was rinsed with a small volume of phosphate buffered saline. The tissue was placed in a beaker four times the size of the volume of the tissue. One- fourth volume trypsin (0.25 mg/ml) and ¼ volume 1.0% bile in HBSS buffer, pH 6.9, was added to the tissue. The pH was adjusted to 6.9 with 1.0M sodium hydroxide, while the solution of tissue was stirred. The tissue was incubated in a 40° C. water bath with trypsin-bile solution for no longer than 30 minutes. The number of merozoites in solution was determined at five minute intervals on a hemacytometer, and was stopped when the release of merozoites remained the same or diminished. The pH was monitored every ten minutes and adjusted to 6.9 with 1.0M sodium hydroxide while rapidly stirring the tissue. The reaction was stopped by adding a volume of 10% bovine serum albumin to 50% BSA of the original volume to tissue suspension, or bovine calf serum to 10%. The pH was adjusted to 7.0– after addition of bovine serum albumin, the tissue was removed, the solution was filtered through cheese cloth, and then through approximately 25 ml nylon wool in a loosely packed 60 ml syringe. The solution was spun at 550×g for 15 minutes, and the pellet was resuspended in a 0.5 ml to 2 ml of HBSS, pH 6.9. The merozoites were washed twice with HBSS. The merozoites were further purified by passing them slowly through a column of nylon wool containing HBSS, pH 6.9, at 37° C. The merozoites moved through the column faster than the debris. The fractions were observed under a microscope to determine which to keep, based upon the amount of debris with them.

About $7.33 \times 10^8$ merozoites were isolated from nine animal tests using the above procedure. The merozoites isolated using the trypsin-bile procedure were able to infect swine testicular cells as well as were the sporozoites.

Infectivity of Merozoites Derived from Pigs or ST Cells

It was established that the merozoites derived from the swine testicular cell culture described above were infectious and virulent in pigs. It was also verified that the swine testicular cell culture derived merozoites were not dramatically altered by passage through the swine testicular cells from the native pig derived merozoites.

Eleven CDCD pigs were randomly separated into three groups. The three pigs in Group 1 received $6.25 \times 10^3$ oocysts. The four pigs in Group 2 received $2 \times 10^5$ animal-derived merozoites isolated from pigs. Group 3, with four pigs, received $2 \times 10^5$ merozoites isolated from swine testicular cells which were inoculated with sporozoites. All pigs were fecaled from day 3 to 10 post infection. Clinical signs were recorded twice a day on each pig. One pig from Group 2 died on day one post infection, and one pig from Group 3 died four days post infection. These pigs were removed from the study.

The results are shown in Table 4.

The pigs in Group 1 all had diarrhea and all shed oocysts greater than 80 per 100×field. Two of the three pigs in Group 2 shed oocysts from 1 to 8 per 100×field, and had diarrhea, while the remaining pig in the group had no diarrhea and shed no oocysts. One pig of the three in Group 3 had clinical signs, while all three pigs shed oocysts from 1 to 11 oocysts per 100×field. This study substantiates that the cell culture derived merozoites are not dramatically altered from the merozoites derived from the pig with respect to cell troposim and pathogenicity.

Infectivity of Free Swimming Merozoites

To determine if tissue culture derived free swimming merozoites are infectious in pigs, two pigs were inoculated with $2.4 \times 10^5$ tissue culture-derived merozoites. Pigs shed viable oocysts days 6, 8 and 9 post challenge, demonstrating that the merozoites harvested from ST cells could infect pigs. The merozoites were cultured in two different media, DMEM+10% serum, and MEM+10% serum. There was no substantial difference in infectivity as a result of the choice of medium.

Enhancement of IgA Titers

The protective *Isospora suis* antigens can be presented to pigs parenterally or by the oral route, resulting in the protection of pigs from challenge with oocysts. We have completed several animal experiments which verify that the oral vaccination of pregnant gilts with the proper *Isospora suis* antigens will result in protection of nursing pigs from a challenge with oocysts (see Table 6). Below is data (see Table 8) that demonstrates that sporozoite and merozoite antigens can be used to boost the lactogenic immunity as evaluated by specific IgA antibody responses. IgA antibody titers were determined using a specific ELISA which measured responses to *I. suis* oocyst lysate. Note that the nonvaccinated controls do have preexisting titers but the protective milk level drops rapidly without the prefarrow boosting. Briefly, eleven pregnant gilts were purchased and randomly assigned into three groups. Group A were designated as nonvaccinated controls, Group B received three IM doses of an oocyst lysate that represented $1.7 \times 10^6$ sporozoites per dose for a total of $5.1 \times 10^6$ sporozoites. Group C received three IM doses of merozoites that represented $1.7 \times 10^6$ merozoites per dose for a total of $5.1 \times 10^6$ merozoites. All IM vaccinations contained Freund's incomplete adjuvant.

The IM vaccinations with the oocyst and merozoite lysates resulted in a four fold increase in the IgA titer in 5-day-milk over the control pigs. Mucosal immunity can be boosted using sporozoite and merozoite antigens as indirectly measured by the lactogenic immune response. This data also indicates that sporozoite, merozoite or a combination of both will be important in developing an effective vaccine against *I. suis* infections. Antigens such as the attachment factor for sporozoites are preferred as immunogens as the antibodies produced against the attachment factor will bind to the sporozoites and prevent initial infection. Antibodies against merozoites(although not capable of preventing infection with sporozoites) should help clear the infection by binding to the free swimming merozoites once released from the infected intestinal cells thus reducing the spread and reducing the morbidity of the disease. These antigens may be presented by either the oral or parenteral routes.

Passive Immunization of Piglets by Maternal Antibodies from Orally Immunized Gilts At birth baby pigs will absorb colostral antibodies and lymphocytes into their blood stream and test seropositive for *I. suis* antigens. This study was designed to determine if these systemically-derived antibodies are protective when compared to the passive antibodies that remain in the milk.

I. Eight pregnant gilts were separated into two groups of four gilts each. Group 1 served as a control group and the gilts were not treated. Group 2 received three oral challenges with $2.0 \times 10^5$, $4.0 \times 10^5$, and $8.0 \times 10^5$ sporulated oocysts at 5, 3, and 1 week prefarrow, respectively. At two days of age, after two full days of nursing, one half of the pigs were removed from each gilt and were placed in seperate isolation units. At five days of age, all of the piglets were orally challenged with $1.5 \times 10^4$ sporulated oocysts. Table 5 shows the results.

The piglets that remained with the dams passively acquired protection from the vaccinated gilts, as compared to the piglets which remained with the control gilts. However, piglets from vaccinated gilts were not passively protected over the control piglets if they were transferred to boxes after only two days of nursing and then inoculated with oocysts when they were five days old. Therefore, the colostrum containing antibodies and white blood cells ingested during the first day of life did not protect pigs when they were removed from the gilt for three days and then inoculated with oocysts.

II. Ten pregnant gilts were randomly separated into three groups.

Group 1 (three gilts), as the control group, was not vaccinated.

Group 2 (four gilts) received three oral challenges with $2 \times 10^6$, $4 \times 10^6$, and $8 \times 10^6$ sporulated oocysts at 5,3, and 1 week prefarrow, respectively.

Group 3 (three gilts) received one oral challenge with $2 \times 10^6$ sporulated oocysts five weeks prefarrow, followed by three intramuscular shots (each $2 \times 10^6$ sporulated oocysts) of a lysate of sporulated oocysts. The oocysts were frozen and thawed three times. The first two shots administered to the gilts were in Freund's Incomplete Adjuvant, followed by the last shot in no adjuvant.

The results are shown in Table 6. Tukey's Honest Significant Difference test was used to analyze the differences between the group means in this experiment. There was no statistical difference between the mean MID (morbibity incidence and duration) values of any of the groups. However, there was a statistical difference between the mortality and the average daily weight gain (ADWG) of each of the vaccinated groups as compared to the controls, at a $p=0.01$ level. These data demonstrate that lactogenic immunity acquired from immunized gilts can protect nursing piglets challenged with *Isospora suis*.

Vaccination of Pregnant Gilts with *Isospora suis* Antigens

Vaccinating pregnant gilts with antigens from *Isospora suis* has protected nursing piglets from a challenge of $1.5 \times 10^4$ sporulated oocysts at a statistically significant level. Three different studies of gilts have been completed to substantiate that sporozoites and/or merozoites derived from pigs or from ST cells can be used effectively as a vaccine.

Six gilts were purchased from a specific pathogen-free herd and were separated into two groups of three gilts each. Each gilt was vaccinated intramuscularly at five, two, and one week pre-farrow. The first group served as a control and was vaccinated with an equivalent amount of swine testicular cell lysate in a concentration corresponding to that which was found in the vaccinated group ($4.5 \times 10^5$ swine testicular cells per gilt per shot). The second group was vaccinated with merozoites that were derived from swine testicular cells. The actual amount of merozoites used for each vaccination was $1.8 \times 10^7$, $2.6 \times 10^6$ and $2.4 \times 10^6$ merozoites per gilt.

Both free swimming and intracellular merozoites were collected. Vaccines in both groups contained Freund's incomplete adjuvant in the first and second vaccinations only. No adjuvant was used in the final vaccination. Blood samples were taken from the gilts prior to their first vaccination, on day of farrowing, and at 21 days post-farrow. Colostrum and milk samples were taken on day of farrow, day of challenge milk (five days post-farrow), and 21 days post-farrow for comparison of the levels of IgG and IgA between each of the treatment groups.

At five days of age, the piglets were orally challenged with $1.5 \times 10^4$ sporulated oocysts per pig. The piglets were weighed at five days of age (Day of challenge), 12 (seven days post-challenge), and 21 days of age. All piglets were bled at five days of age and 21 days of age. Clinical signs were recorded daily. The percent morbidity, percent morbidity incidence and duration (MID=number of days with pigs showing clinical signs/total number of pig days$\times$100), average mortality and average daily weight gains (ADW) were calculated for each litter.

There were at least 23 piglets in each of the control and merozoite vaccinated group. Table 7 summarizes the data collected from this study.

Mann-Whitney U statistic test was used to analyze the differences between the group means in this experiment. although the vaccinates gained weight at a daily rate that was 47% better than the controls and had a reduced morbidity incidence and duration value of 13% as compared to the controls, there was no statistical difference between groups.

However, there was a statistical difference between the mean percent thmortality of the vaccinated groups as compared to the controls, at a p=0.05 level. These data demonstrate that the cell culture derived merozoites can be used to vaccinate sows in order to passively protect nursing piglets challenged with *Isospora suis*.

Merozoites derived from the inoculation of swine testicular cells with sporozoites can effectively reduce the effects of a challenge of $1.5 \times 10^4$ sporulated oocysts to five day old nursing piglets. The use of sporozoite antigen or antigens with merozoites may more effectively control the effects of this disease in pigs. Therefore, the dose of these antigens together will vary from what is effective when sporozoite antigen or antigens or merozoites are used alone.

Isolation of Monoclonal Antibodies to Sporozoites and Merozoites

Monoclonal antibodies which can inhibit (neutralize) the infection of sporozoites into swine testicular cells were prepared as described below. Oocysts from fecal material were purified and then freeze-thawed three times to lyse the sporozoites.

Four mice were vaccinated with 50 micrograms of oocyst lysate in Freund's Complete Adjuvant in equal amounts IM and IP. Four weeks later the mice were boosted with 50 micrograms of oocysts lysate in Freund's incomplete adjuvant in equal amounts IM and IP. Just prior to the third vaccination, the mice were bled through the tail, and serum was collected. The serum was used as a probe for an immunoblot using oocyst lysate. The mouse that responded best to the first two vaccinations was used for the fusion. The third vaccination was completed three weeks after the second vaccination by injecting 50 micrograms of oocysts lysate intravenously via the tail vein. The mice were sacrificed 3 days after the third aqueous vaccination and the fusion was completed as described below.

The spleens were removed and their B-cells harvested. Splenocytes ($4 \times 10^7$ cells) and fusion partners ($4 \times 10^7$ SP2/0 cells) were centrifuged together at 200×g for 8 min., and the supernalant was removed. Polyethylene glycol, followed by DMEM, were added dropwise, and the mixture allowed to set. The mixture was centrifuged and HAT medium, which kills unfused cells, was added. The mixture was distributed by pipette into the wells of microtiter plates.

The hybridomas were screened using a sporozoite/oocyst lysate and/or merozoite Enzyme-Linked Immunosorbent Assay (ELISA). Microtiter plates were coated with a desired dilution of oocyst lysate or merozoite lysate and incubated overnight at 4° C. The plates were washed with phosphate buffered saline plus Tween-20 and non-bound sites were blocked with 10% fetal bovine serum. Plates were washed again as before and inoculated with 2- to 4-fold dilutions of hybridoma supernatant fluid. As a negative control, one column was inoculated with 2- to 4-fold dilutions of conditioned media used to support the growth of the hybridomas. After incubation for 1-hour at room temperature, the plates were washed with phosphate buffered saline plus Tween-20 and horseradish peroxidase-labeled goat anti-mouse IgG was added. Following incubation at room temperature for 1-hour, the plates were washed with phosphate buffered saline plus Tween-20 and ABTS substrate was added to each well. After incubation in the dark for 30 minutes, plates were read on an ELISA plate reader with a 405 nm filter. A positive reading was determined by samples giving a specific color reaction $\geq 0.2$ optical density unit. Primary hybridoma clones were produced and approximately 600 of them were screened using the ELISAs described above. Five primary hybridomas were positive and were screened using an immunoblot with oocyst lysate proteins. Two primary hybridomas, 2G3 and 1E2, were chosen for the isolation of clones. Twenty-seven clones were isolated from 2G3 primary hybridoma and two clones were isolated from 1E2 primary hybridoma. Sporozoite and merozoite ELISAs and western blots were used to confirm that all of the 27 clones isolated from 2G3 primary hybridoma were secreting antibodies that reacted with sporozoite proteins, but not merozoite proteins. Sporozoite and merozoite ELISAs again were used to confirm that neither of the clones isolated from 1E2 primary hybridoma were secreting antibodies that reacted with sporozoite or merozoite proteins. It was decided to use 2G3 primary hybridoma to begin the cloning process from which the mab of choice was derived: 2G3H7 and hereafter referred to as AmH7.

Development of an Assay to Detect Neutralizing Sporozoite Antibodies

Swine testicular cells were grown to confluency in Leighton slides or microtiter plates (48 or 96 well). Confluent swine testicular cells were rinsed 3 times with a basal medium, such as Dulbecco's or Eagle's Modified Essential Medium. Sporozoites were prepared in basal media plus 1% to 10% bovine calf serum, with 4% preferred. Serial dilutions of fluids to be tested were done in basal media. Fluids containing antibodies, including, but not limited to, serum from pigs and gilts, colostrum and milk from gilts, sporozoite hyperimmune serum from guinea pigs and goats, merozoite hyperimmune serum from guinea pigs and goats, and/or monoclonal antibodies have been tested. To each serum dilution an equal volume of sporozoites was added and were incubated for 60 minutes at 37° C. A negative control serum was also incubated in the same manner. The sporozoite-serum mixtures were then inoculated into the ST cells and allowed to absorb for 90 minutes. Cells were rinsed three times with basal media and incubated at 37° C. Sporozoites incubated with negative control serum or samples that did not contain neutralizing antibodies to sporozoites were able to replicate in the swine testicular cells, causing cytopathic effect throughout the cells. Sporozoites incubated with fluids containing neutralizing antibodies significantly reduced or completely eliminated infection in the swine testicular cells. The reduction of sporozoite infection, and thus the amount of cytopathic effect observed, is dependent upon the ratio of neutralizing antibodies to sporozoites.

Identification of Sporozoite Neutralizing Monoclonal Antibodies

A monoclonal antibody has been isolated which is specific for sporozoites, and it has been demonstrated that a monoclonal antibody can neutralize the infectivity of sporozoites in swine testicular cells.

Anti-*I. suis* sporozoite monoclonal antibody AmH7 was shown to inhibit the infectivity of sporozoites for swine testicular cells. The sporozoites were incubated with monoclonal antibody H7 for one hour, and then added to swine testicular cells.

The ST cells were not infected with sporozoites after seven days, whereas cells treated with sporozoites in negative control serum or basal medium alone showed cytopathic effect caused by sporozoite infection.

Protective antigens are antigens that when added in a vaccine result in the reduction of the severity of the infection in the vaccinated pig after it is challenged with *Isospora suis* sporulated oocysts. The protective *Isospora suis* proteins were identified by four different methods:

(1) Immunoblot analysis of proteins from sporozoites and merozoites was the first method used to assist in identifying antigens of potential vaccine importance (protective sporozoite antigens). The probe used in this immunoblot was milk collected from a gilt which protected her piglets from a challenge of $1.5 \times 10^4$ sporulated oocysts. Four sporozoite proteins were recognized, having molecular weights of 110, 100, 54.5 and 37.5 kDa. The most intense band was the 37.5 kDa band.

(2) Neutralizing monoclonal antibody AmH7 was used as a probe in an immunoblot to identify the sporozoite protein with which it reacts, using either a denaturing or non-denaturing gel. The proteins from five micrograms of sporozoite and merozoite lysates were separated on a 4 to 16% gradient gel containing SDS. The proteins were transferred to a membrane and an immunoblot was completed using the Mab-H7 as a probe. Two intense bands were observed, which had an estimated molecular weight of about 218 and 207 kDa. The other two bands had molecular weights of 190 and 180 kDa. The intense bands of 218 and 207 kDa were also seen when milk obtained from a gilt which had been challenged with three oral doses of oocysts prior to farrowing, and subsequently protected her piglets from oocysts, was used as a probe. These two bands may represent different glycosylation variants of the same protein. Two proteins that have molecular weights of 170 to 220 kDa.

(3) Identification of sporozoite surface proteins using a biotin labeling system. The surface proteins of sporozoites are labeled with a biotin complex that labels specific amino acids of the surface proteins. A lysate of the labeled sporozoite preparation is made and subsequently run on a denaturing gel. The proteins are transferred to a membrane and the sporozoite surface proteins are identified using a streptavidin-alkaline phosphatase system or a chemiluminescence substrate. The molecular weights of the proteins are then determined.

(4) Specific Immunofluorescence was conducted using sporozoites and the AmH7 mab. Fluorescence was observed to be at the apical end of the sporozoite the site of attachment of the sporozoite to cell culture. Thus demonstrating that the mab AmH7 is directed to the attachment protein.

The hybridoma producing monoclonal antibody AmH-7 was deposited as "AmH7 Pass 10" with the American Type Culture Collection, Manassas, Va., USA on Jun. 7, 1995, under accession no. HB 11930.

An Indirect Immunoflourescent Antibody Assay (IFA) was completed with the sporozoites using Mab AmH7. Sporozoites were fixed onto pre-cleaned glass slides with methanol. Mab AmH7 as well as a negative control that contained the media that hybridoma AmH7 was grown in were incubated with the sporozoites for 30 minutes at 37° C. in a humidified chamber, washed, and then incubated with Goat anti-mouse FITC-labeled conjugate as previously described. The slides were washed and coverslips were then mounted on the slides which were examined using fluorescence microscopy. It was demonstrated that Mab AmH7 is specific for the outer membrane (plasma membrane and/or the cortical cytomembrane) with increased intensity in fluorescence at one end of the sporozoite, most likely the apical complex (consisting of the conoid and polar rings). Fluorescence was also seen 'speckled' throughout the sporozoite, appearing as 'granules', possibly the micronemes and/or amylopectin granules. The nucleus did not fluoresce. Increased dilutions of Mab AmH7 resulted in the fluorescence of only one end of the sporozoite, most likely the apical complex.

Isolation of Genes coding for *Isospora suis* Proteins

Production of Sporozoite and Merozoite cDNA Libraries

Isolation of mRNA from Oocysts

Oocysts ($1 \times 10^8$) were isolated from the feces of challenged pigs and purified as described previously. The total oocyst RNA was isolated using a kit purchased from Stratagene, which uses guanidium thiocyanate-phenol to isolate the RNA. The oocysts were ruptured using siliconized glass beads. A Promega kit was used to isolate the poly-A mRNA from the total RNA. This kit uses a unique system of biotinylate oligo (dt) to bind to the poly-A-mRNA and streptavidin mangesphere™ in combination with a MagneSphere™ magnetic separation stand to isolate the poly-A mRNA.

The cDNA library was made using a ZAP Express cDNA Synthesis Kit from Stratagene. This process includes adding an EcoRI site on the 5' end of the cDNA, and a Xho I site on the 3' end of the mRNA. This allows the cDNA to be placed in the vector in the correct orientation, thus requiring one-half the number of clones in the library. This system also has the ability to express the cDNA in bacterial or mammalian cells. The cDNA from the sporozoite was ligated into the vector called ZAP Express XR, and packaged with a packing extract from Stratagene called Gigapack Gold.

For a further discussion of this technique, please refer to U.S. Pat. No. 5,128,256, the entire contents of which are hereby incorporated by reference.

The merozoite cDNA library was made from RNA isolated from pig-derived merozoites, as described above. The cDNA library was made using a kit purchased from Stratagene.

Isolating the Gene Coding for the Sporozoite Attachment Factor

For primary screening of the sporozoite and merozoite cDNA library, AmH7 was used. The libraries were screened as follows:

(A) Preliminary testing by pre-absorbing antibody (AmH7) with *E. coli*/phage lysate and confirming that the primary antibody can detect nanogram quantities of the antigens using a dot immunoblot. The lowest dilution of antibody detected by antigen was determined.

(B) The titer of the library was reconfirmed following the exact procedure used when the library was plated.

(C) Incubate $4-5 \times 10^4$ phage with 600 μl of *E. coli* cells that have an OD=⅔ at 600 nm for fifteen minutes at 37° C. Plate out in 7.5 ml top agar on 150 mm pre-dried plates. Incubate for about 3.5 hours until small plaques become visible.

(D) Pre-incubate PVDF membrane with IPTG as described by Stratagene.

(E) Place filters on plates and place plates at 37° C. for 3.5 hours. The filters were oriented with the plates by a needle and dye.

(F) Prepare a second filter by removing the first filter and placing another filter on the plates. Incubate plate with second filter for four hours at 37° C. Place the first filter in the blocking solution while waiting for the second one to grow.

(G) Block filters overnight.

(H) Incubate filters for 45 minutes with correct dilution of AMH7 (absorbed against *E. coli* phage lysate) in blocking buffer.

(I) Wash filters, and incubate filters for 45 minutes with the correct dilution of biotin labeled goat anti-mouse IgG (heavy and light chain specific).

(J) Wash filters, and incubate filters with the correct dilution of Peroxidase-labeled streptavidin.

(K) Wash filters, and incubate filters in TMB (3, 3'0.5, 5'-tetramethylberizidine) peroxidase substrate system purchased from Kirkegaard & Perry Laboratories, Inc. for several minutes.

(L) Pick positive colonies found on both filters from each plate and place agar with plaques in phage stability media overnight.

(M) Titer each positive plague from the first screening.

(N) Repeat the above process, but this time plate out 1000 phage per plate.

(O) Complete third round of screening with 100 phage per plate. All phage should be positive from this screening.

*Isospora suis* cDNA (phage clone 4-1-1 containing the *Isospora suis* DNA) were subcloned into a vector containing the CMV promoter. This DNA clone was isolated and characterized, and large quantities of the DNA clone was produced (identified here as pBK CMV 411).

All of the monoclonal antibody produced to the *Isospora suis* lysate recognizes the same protein that is encoded by the clone 411. Furthermore, the sow milk which identified MW proteins of 218 Kd-207 Kd, 110 Kd, 100 Kd, 54.5 Kd, and 37.5 Kd proteins also recognized the proteins encoded by clone 411. Likewise, specific anti sera derived from guinea pigs immunized with oocyst lysate which identified MW proteins of 180–170 Kd, 87–84 Kd by western blot analysis also reacted with the protein encoded by clone 411, whereas antisera derived from merozoite immunized guinea pig (identifying MW protein bands of 53–43 Kd) did not react with protein.

Mice were injected with plasmid DNA (pBK CMV 411) containing the desired gene under the control of the CMV promoter. The cDNA library made using a Stratagene ZAP Express cDNA kit uses a vector which contains the CMV promoter. Therefore, all of the plasmids isolated from this library using antibodies can be expressed by direct injection into mice. One hundred micrograms of the desired test plasmid was injected into the hind leg muscle of mice (25 μg per injection site: two injection sites per leg). The mice were boosted by two additional injections two to three weeks apart. The serum was obtained two weeks later from the blood. The serum isolated from the mice contained antibodies which had properties similar to the neutralizing Mab-H7. Therefore, the genes isolated coded for the desired proteins. DNA may be sequenced in a conventional manner by the methods of Sanger, et al. It is preferable that, prior to sequencing, the DNA of interest be purified, and/or amplified (e.g., by PCR or by intracellular replication) as this will reduce the chance of a sequencing error. If a sequencing error is suspected—e.g., because when the sequenced DNA is synthesized and used to express a protein, the encoded protein lacks the expected activity or because the translated amino acid sequence is inconsistent with the data characterizing the natural protein supposedly encoded by the DNA—the DNA may be resequenced in a manner likely to identify the error. For example, both strands may be individually sequenced, and the results compared for complementarity. Alternatively, or additionally, the DNA may be restricted using a restriction enzyme, and one or both strands of the fragments sequenced. For further assurance, the DNA may be restricted into different fragments using a second enzyme with a different recognition site, and sequencing repeated.

Figure 1B:
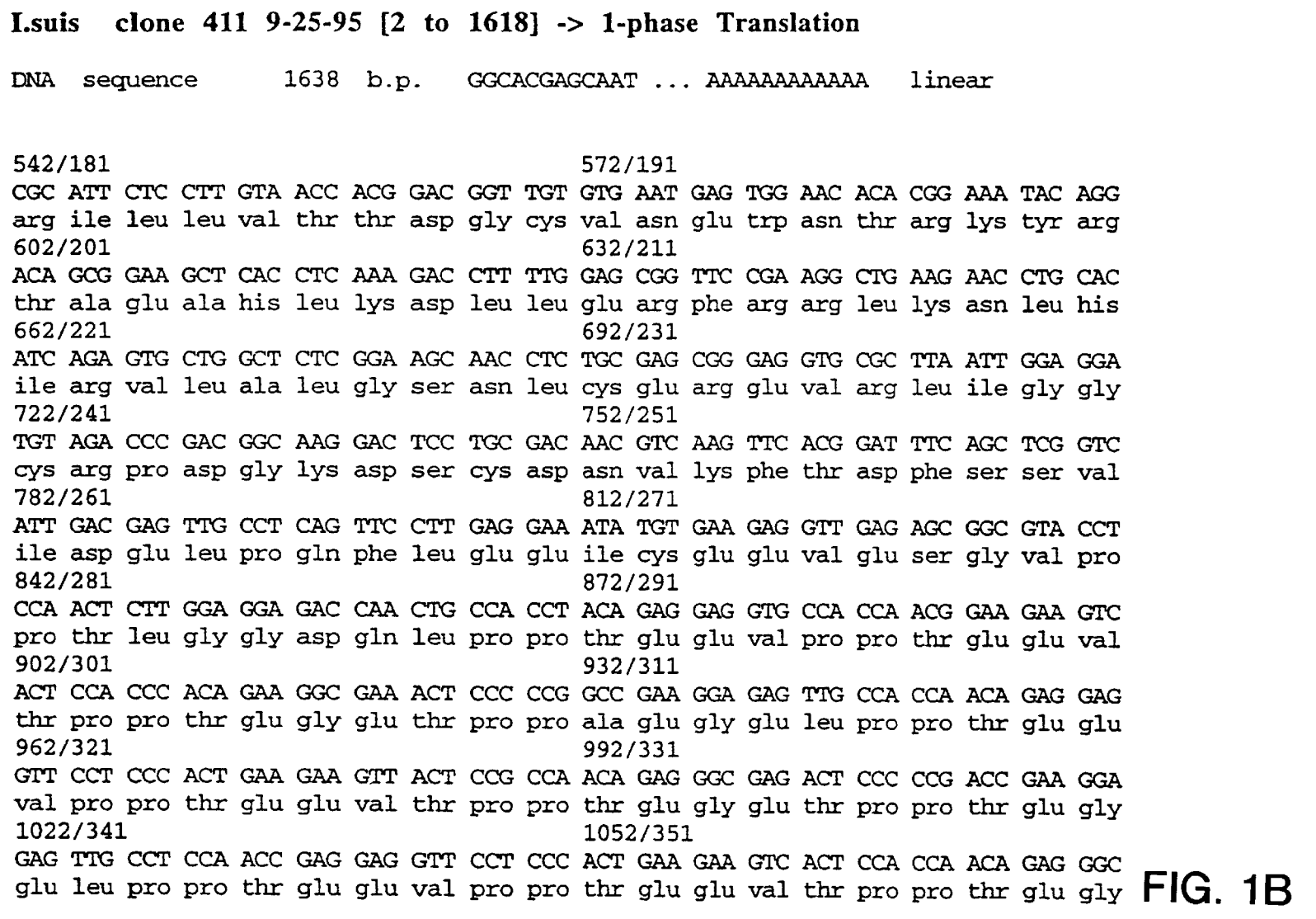
Figure 1C:
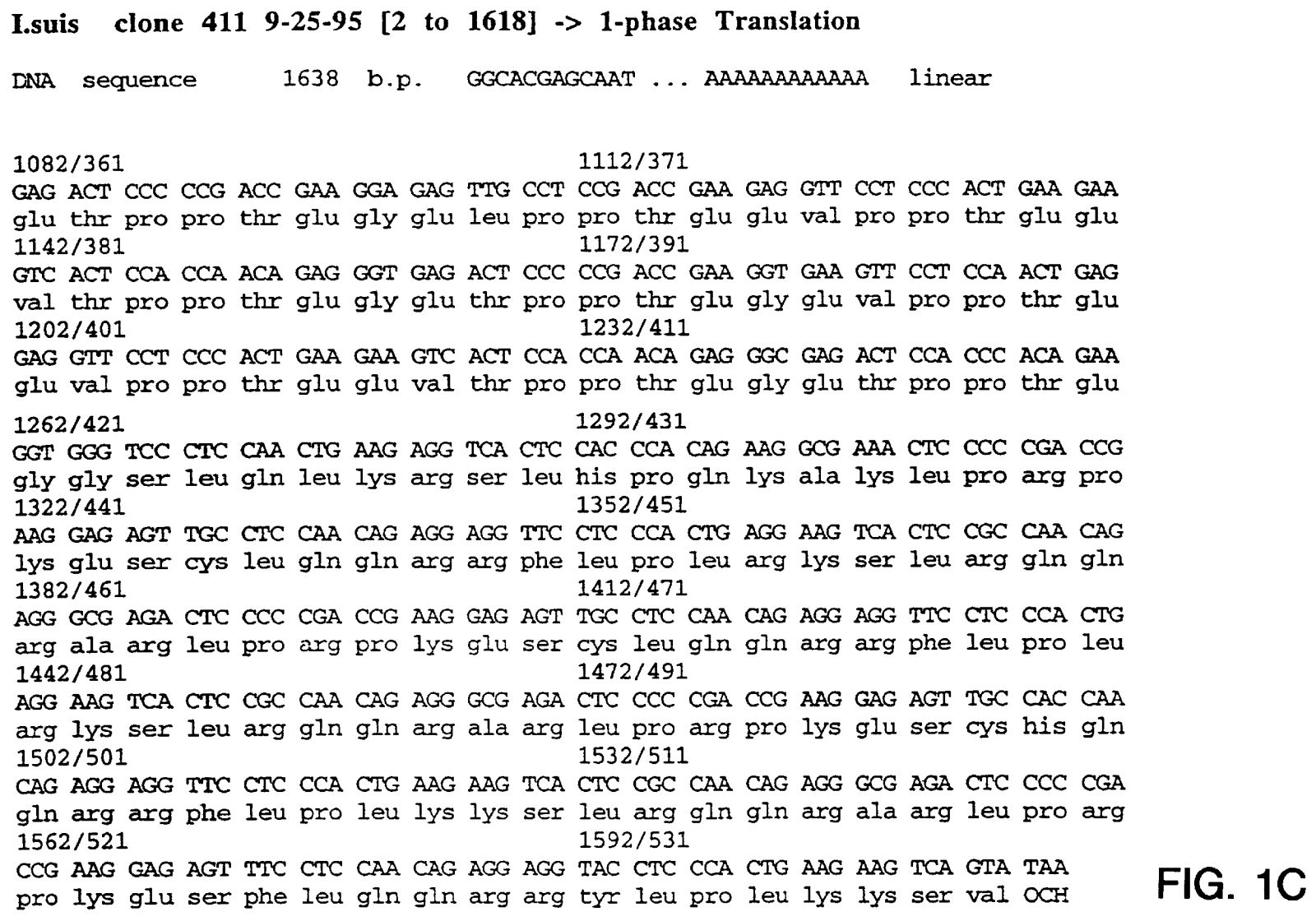
Figure 3B:
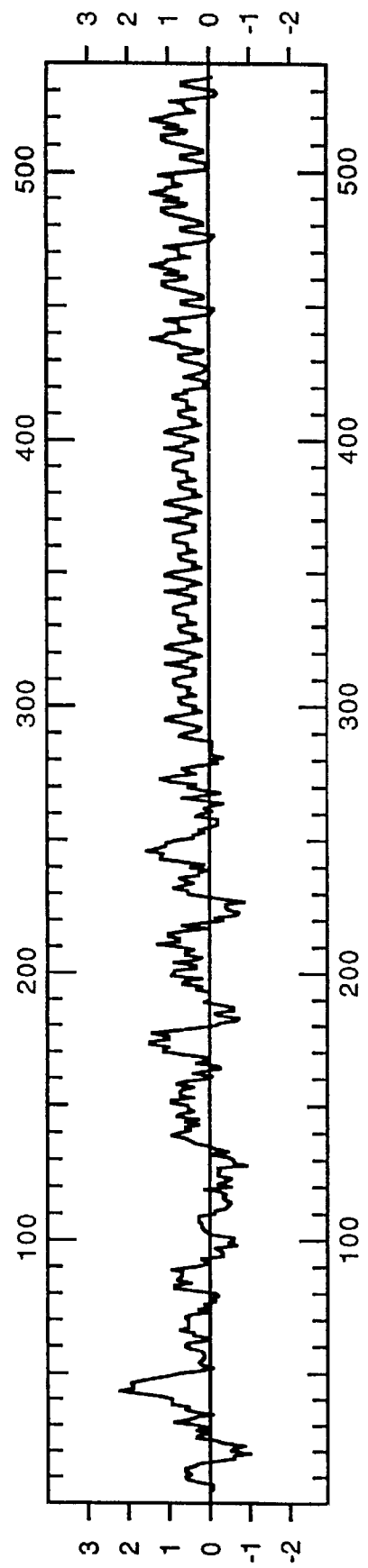

The sporozoite attachment factor is composed of one or more proteins, one of which is identified herein as sporozoite attachment protein-1 (SAP-1). The 3' DNA sequence for the SAP-I gene is shown in FIG. 1 (SEQ ID NO:1) and the corresponding amino acid sequence in FIG. 2 (SEQ ID NO:2). A hydrophilicity plot is shown in FIG. 3B. The SAP-1 DNA sequence does not encode the entire protein, However, a full length cDNA may be isolated as described below.

The 5' portion of the SAP-1 gene will be isolated using either inverse PCR methods as described in Biotechniques Vol. 17,No 6 (1994) pages 1051–1053 or using commercial kits available using RACE: Rapid amplification of cDNA Ends as described in PCR protocols, chapter 4 pages 28–38. Academic press copyright 1990, authors Michael A. Innis, David H. Gelfand, John J. Sninsky, and Thomas J. White.

Briefly mRNA will be isolated from oocyst material as previously described. This material will be used to make cDNA as previously described and circularized by ligating with T4 DNA ligase. Specific 5' and 3' oligos corresponding to known sequence contained in clone 411 will then be used with PCR to amplify the 5' end of the gene through inverse PCR. The isolated mRNA will also be used in a northern analysis using probes derived from the 411 clone.

Immunogenicity of Sporozoite Attachment Protein. Encoded by SAP-1 gene on Plasmid pBK-CMV 411, in Pigs.

Animal studies were conducted in young gnotobiotic pigs. A total of nine pigs were used in this study. The objectives of this study were to examine the immunogenicity of sporozoite-attachment protein plasmid PBK-CMV 411 (SAP 411 plasmid) and to evaluate its potential as a vaccine. Two pigs were nonvaccinated controls, three were vaccinated IM with 500 $\mu$g's of SAP 411 plasmid at 5 and 15 days of age and four were vaccinated IM as above and orally fed 1 ml an *E. coli* lysate containing the SAP at 15 and 22 days of age. Pigs were orally challenged with $1.6\times10^4$ sporulated oocysts at 30 days of age. Pigs were bled on the day of the first vaccination, day of challenge and at 14-days after challenge (end of test). One pig from each group was sacrificed five days after challenge. The small intestine was removed and the total number of merozoites counted using the procedure described previously.

The SAP induced an immunogenic response as evaluated by Western blot analysis (Table 9). Antibodies to the SAP were observed in the post-vaccination sera of pigs injected with the SAP 411 plasmid. The number of merozoites recovered from the vaccinated groups was significantly reduced compared to the control sacrificed pig. A 96% reduction was seen in the IM only vaccinated group and a 99% reduction was seen in the IM/oral group. This reduced number of merozoites would indicate that the SAP 411 plasmid was effective in reducing the infectious stages of *I.* suis. This finding was consistent with work that had previously been completed where animals were challenged three times with sporulated oocysts in order to make them naturally immune to *I. suis*. Pigs were sacrificed 5-days after the third challenge and the number of merozoites recovered from the small intestine were similar to the amount recovered from the SAP 411 plasmid vaccinated animals. The efficacy of SAP 411 plasmid was further confirmed by the observation of nonviable oocysts in post-challenge fecals collected from the vaccinated animals.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

TABLE 1

| Study | Group | Route pre-farrow | Time | Dose | Antigen | Response in nursing pigs |
|---|---|---|---|---|---|---|
| 1 | 1 | oral | 5 | $1.6 \times 10^6$ | spz | protected |
|   |   | oral | 3 | $3.2 \times 10^6$ | spz |   |
|   |   | oral | 1 | $6.4 \times 10^6$ | spz |   |
| 1 | 2 | oral | 5 | $1.6 \times 10^6$ | spz | protected |
|   |   | IM | 4 | $2.4 \times 10^7$ | spz |   |

TABLE 1-continued

| Study | Group | Route pre-farrow | Time | Dose | Antigen | Response in nursing pigs |
|---|---|---|---|---|---|---|
|   |   | IM | 3 | $3.2 \times 10^7$ | spz |   |
|   |   | IM | 1 | $3.6 \times 10^7$ | spz |   |
| 2 | 1 | oral | 5 | $1.6 \times 10^6$ | spz | protected |
|   |   | IM | 4 | $1.6 \times 10^7$ | spz |   |
|   |   | IM | 3 | $1.6 \times 10^7$ | spz |   |
|   |   | IM | 1 | $1.6 \times 10^7$ | spz |   |
| 2 | 2 | IM | 5 | $1.6 \times 10^7$ | spz | protected, but |
|   |   | IM | 3 | $1.6 \times 10^7$ | spz | less than |
|   |   | IM | 1 | $1.6 \times 10^7$ | spz | group 1 |
| 2 | 3 | IM | 5 | $1.6 \times 10^7$ | mz | protected, but |
|   |   | IM | 3 | $1.6 \times 10^7$ | mz | less than |
|   |   | IM | 1 | $1.6 \times 10^7$ | mz | group 1 |
| 2 | 4 | IM | 4 | $1.6 \times 10^7$ | spz + mz | protected, but |
|   |   | IM | 3 | $1.6 \times 10^7$ | spz + mz | less than |
|   |   | IM | 1 | $1.6 \times 10^7$ | spz + mz | group 1, but > Groups 2 & 3 |
| 3 | 1 | IM | 5 | $1.8 \times 10^7$ | CCdmz | Protected |
|   |   | IM | 3 | $2.6 \times 10^6$ | CCdmz |   |
|   |   | IM | 1 | $2.4 \times 10^6$ | CCdmz |   |
| 4 | 1 | IM | 5 | $1.0 \times 10^7$ | CCdmz | Protected |
|   |   | IM | 3 | $2.0 \times 10^7$ | CCdmz |   |
|   |   | IM | 1 | $3.0 \times 10^7$ | CCdmz |   |

TABLE 2

| Vaccine | Animal | Antigen | Route | Unit Range for a MED | Time |
|---|---|---|---|---|---|
| 1 | Preg. Sow | SAP[a] | parenteral | $1 \times 10^5$–$1 \times 10^9$ | 5, 3, 1 |
| 2 | Preg. Sow | SAP | oral[b] | $1 \times 10^5$–$1 \times 10^9$ | 5, 3, 1 |
| 3 | Preg. Sow | SAP | parenteral + oral[b] | $1 \times 10^5$–$1 \times 10^9$ | 5, 3, 1 |
| 4 | Preg. Sow | SAP | parenteral | $1 \times 10^5$–$1 \times 10^9$ | 5, 3, 1 |
|   |   | CCdMZ | oral | $1 \times 10^5$–$1 \times 10^9$ | 5, 3, 1 |
| 5 | Preg. Sow | SAP | oral | $1 \times 10^5$–$1 \times 10^9$ | 5, 3, 1 |
|   |   | CCdMZ | oral | $1 \times 10^5$–$1 \times 10^9$ | 5, 3, 1 |
| 6 | Preg. Sow | SAP | parenteral + oral | $1 \times 10^5$–$1 \times 10^9$ | 5, 3, 1 |
|   |   | CCDMZ | parenteral + oral | $1 \times 10^5$–$1 \times 10^9$ | 5, 3, 1 |
| 7 | Preg. Sow | CCdmZ | parenteral | $1 \times 10^5$–$1 \times 10^9$ | 5, 3, 1 |
| 8 | Preg. Sow | CCdMZ | oral | $1 \times 10^5$–$1 \times 10^9$ | 5, 3, 1 |
| 9 | Preg. Sow | CCdMZ | parenteral + oral | $1 \times 10^5$–$1 \times 10^9$ | 5, 3, 1 |

[a]SAP = Sporozoite attachment protein. One unit of SAP is equal to concentration of SAP in each sporozoite.
[b]The oral route of vaccination may require an encapsulated SAP to protect this antigen from the stomach fluids. Delivery of the SAP by bacteria would also serve to protect the SAP.
[c]CCdmz = Cell-Culture-derived merozoites. A unit of this antigen is defined as type 1 or type 2 merozoite.

TABLE 3

| Vaccine | Animal | Antigen | Route | Unit Range for a MED[4] | Time-Age[e] in days |
|---|---|---|---|---|---|
| 10 | pig | SAP[a] | parenteral | $1 \times 10^5$–$1 \times 10^9$ | 7, 17 |
| 11 | pig | SAP | oral[b] | $1 \times 10^5$–$1 \times 10^9$ | 7, 17 |
| 12 | pig | SAP | parenteral + oral[b] | $1 \times 10^5$–$1 \times 10^9$ | 7, 17 |

TABLE 3-continued

| Vaccine | Animal | Antigen | Route | Unit Range for a MED[d] | Time-Age[e] in days |
|---|---|---|---|---|---|
| 13 | pig | SAP | parenteral | $1 \times 10^5 - 1 \times 10^9$ | 7, 17 |
|  |  | CCdMZ[c] | parenteral | $1 \times 10^5 - 1 \times 10^9$ | 7, 17 |
| 14 | pig | SAP | oral | $1 \times 10^5 - 1 \times 10^9$ | 7, 17 |
|  |  | CCdMZ | oral | $1 \times 10^5 - 1 \times 10^9$ | 7, 17 |
| 15 | pig | SAP | parenteral + oral | $1 \times 10^5 - 1 \times 10^9$ | 7, 17 |
|  |  | CCdMZ | parenteral + oral | $1 \times 10^5 - 1 \times 10^9$ | 7, 17 |
| 16 | pig | CCdMZ | parenteral | $1 \times 10^5 - 1 \times 10^9$ | 7, 17 |
| 17 | pig | CCdMZ | oral | $1 \times 10^5 - 1 \times 10^9$ | 7, 17 |
| 18 | pig | CCdMZ | parenteral + oral | $1 \times 10^5 - 1 \times 10^9$ | 7, 17 |

[a]SAP = Sporozoite attachment protein. One unit of SAP is equal to concentration of SAP in each sporozoite.
[b]The oral route of vaccination may require an encapsulated SAP to protect this antigen from the stomach fluids. Delivery of the SpzAP by bacteria would also serve to protect the SAP.
[c]CCdmz = Cell-Culture-derived merozoites. A unit of this antigen is defined as type 1 or type 2 merozoite.
[d]the dose is the number of sporozoites or equivalents
[e]in weeks pre-farrowing

TABLE 4

| Group | Infected with | Dose | Pigs with Diarrhea | Shed |
|---|---|---|---|---|
| 1 | oocysts | $6.25 \times 10^3$ | 3/3 | 3/3 |
| 2 | pig mz | $2 \times 10^5$ | 2/3 | 2/3 |
| 3 | ST mz | $2 \times 10^5$ | 1/3 | 3/3 |

TABLE 5

Post-Challenge Results

| Group | ADWG[1] | % Mortality | MID[2] |
|---|---|---|---|
| Control Gilt | −0.03 | 38 | 65 |
| Control Isolated | +0.04 | 19 | 34 |
| Vaccinated Gilt | +0.23 | 22 | 39 |
| Vaccinated Isolated | +0.04 | 23 | 55 |

[1]ADWG: Average Daily Weight Gain from day of challenge.
[2]MID: Morbidity Incidence and Duration

TABLE 6

| Gilt | Treatment | MID* | Group MID | Mort. | Group Mortality | ADWG | Group ADWG |
|---|---|---|---|---|---|---|---|
| Grp 1 |  |  |  |  |  |  |  |
| 123 | Control | 73 |  | 100 |  | −0.04 |  |
| 82 |  | 62 | 68 | 40 | 70 | 0.01 | −0.01 |
| 124 |  | — |  | — |  |  |  |
| Grp 2 |  |  |  |  |  |  |  |
| 830 | Oocysts | 79 |  | 13 |  | 0.19 |  |
| 789 | Oral (3x) | 90 |  | 18 |  | 0.16 |  |
| 119 |  | 5 | 55 | 0 | 8 | 0.33 | 0.23 |
| 118 |  | 45 |  | 0 |  | 0.23 |  |
| Grp 3 |  |  |  |  |  |  |  |
| 122 | Oocysts | 57 |  | 0 |  | 0.27 |  |
| 89 | Oral (1x) | 40 | 47 | 0 | 0 | 0.22 | 0.23 |
| 121 | IM (4x) | 43 |  | 0 |  | 0.20 |  |

*MID is calculated by starting 4 days post challenge; the period in which the first clinical signs are observed.
**ADWG was determined from the day of challenge to 9 days post challenge.

TABLE 7

| Group | Litter | ADWG[a] | Group ADWG | MID[b] | Group Aver. MID | MI*[c] | Mort[d] | Group Arg Mort |
|---|---|---|---|---|---|---|---|---|
| control | 1 | 0.097 | 0.23 | 79 | 80 | 100 | 55 | 43 |
|  | 2 | 0.298 |  | 79 |  | 100 | 50 |  |
|  | 3 | 0.295 |  | 80 |  | 100 | 25 |  |
| merozoite | 4 | 0.351 | 0.31 | 71 | 70 | 100 | 20 | 16 |
|  | 5 | 0.357 |  | 59 |  | 100 | 14 |  |
|  | 6 | 0.214 |  | 80 |  | 100 | 13 |  |

*numbers based on percent
[a]average daily weight gain
[b]morbidity incidence and duration
[c]morbidity incidence
[d]mortality %

TABLE 8

| Grp | Gilts | Antigens used for Vaccination | Routes | Frequency Prefarrow weeks | Colostral IgA titer (Average) | 5-day Milk IgA titer (Average) |
|---|---|---|---|---|---|---|
| A | 4 | None | | | 25 | 5 |
| B | 3 | Oocyst lysate | IM | 5, 3 & 1 | 64 | 20 |
| C | 4 | Merozoite lysate | IM | 5, 3 & 1 | 40 | 20 |

TABLE 9

| | Western Blot Analysis | | Merozoite Isolation |
|---|---|---|---|
| Treatment | PreVac | PostVac | (% Reduction) |
| Nonvaccinated Control | Neg. | Neg. | $5 \times 10^7$ |
| SAP 411 plasmid IM | Neg. | Pos. | $2.5 \times 10^6$ (96%) |
| AP 411 plasmid IM & oral SAP lysate | Neg. | Pos. | $8.25 \times 10^5$ (99%) |
| NonVaccinated Control | ND[1] | ND | $1.8 \times 10^7$ to $7 \times 10^8$ |
| Naturally Immune | ND | ND | $6 \times 10^6$ to $1 \times 10^7$ (94 to 99%) |

[1]ND: Not Done

What is claimed is:

1. A purified antigen which comprises at least one epitope of a sporozoite attachment protein of *Isospora suis* wherein the at least one epitope has an amino acid sequence selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

2. The antigen of claim 1, wherein the sporozoite attachment protein comprises the amino acid sequence of SEQ ID NO:2.

3. The antigen of claim 1, comprising at least two epitopes selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

4. The antigen of claim 1, comprising at least four epitopes selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

5. The antigen of claim 1, comprising at least six epitopes selected from the group consisting of SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1638 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GGCACGAGCA  ATAGCCGGGT  GCAATCCCGG  AGATGAGAGT  CCTTGCCAAA  GCTTGGTACT    60
CGCCTCGTGG  GATACACTGG  AACAGCGCGT  CTTTCAAGCT  GAAGACCAGC  TATGTGAAGC   120
GGCCAGAGAG  GAGGAGAAAG  AAATGCAAAA  TCAGCAGCCC  AGCGTACAGG  AACCAGCGCC   180
GCCATCCAAA  ACAACATGCA  CCAAAGGGCG  AATTGACACC  GCCGCTGTCC  TGGATGGCTC   240
TGGAAGTCTT  AGTCGAAAGG  ACTGGAAAGC  CACTCTGGAG  ATCGCTGACC  TGTTTGCGGG   300
CGCCCTGAAT  ATTGATGAAG  CTGGCAGTCA  CATGAGCGTG  GTGCGCTTCG  CTACAAGCGC   360
GACAACGGAG  TGGGGCCTTC  TGGATCCTGT  GTCTTGGACA  CCGGCAAAGT  TGAAACAACG   420
CATTTCACGT  CTGAGTCATC  CCCGTGGAAG  AACTAACACT  CCGAAAGGTC  TCGAAGAGGC   480
GTACCGCATA  CTTGTTGAAT  CCATGAATAA  GCACCACGAT  GAAGATGCAG  AGAACGTTCA   540
TCGCATTCTC  CTTGTAACCA  CGGACGGTTG  TGTGAATGAG  TGGAACACAC  GGAAATACAG   600
GACAGCGGAA  GCTCACCTCA  AAGACCTTTT  GGAGCGGTTC  CGAAGGCTGA  AGAACCTGCA   660
CATCAGAGTG  CTGGCTCTCG  GAAGCAACCT  CTGCGAGCGG  GAGGTGCGCT  TAATTGGAGG   720
ATGTAGACCC  GACGGCAAGG  ACTCCTGCGA  CAACGTCAAG  TTCACGGATT  TCAGCTCGGT   780
CATTGACGAG  TTGCCTCAGT  TCCTTGAGGA  AATATGTGAA  GAGGTTGAGA  GCGGCGTACC   840
TCCAACTCTT  GGAGGAGACC  AACTGCCACC  TACAGAGGAG  GTGCCACCAA  CGGAAGAAGT   900
CACTCCACCC  ACAGAAGGCG  AAACTCCCCC  GGCCGAAGGA  GAGTTGCCAC  CAACAGAGGA   960
GGTTCCTCCC  ACTGAAGAAG  TTACTCCGCC  AACAGAGGGC  GAGACTCCCC  CGACCGAAGG  1020
AGAGTTGCCT  CCAACCGAGG  AGGTTCCTCC  CACTGAAGAA  GTCACTCCAC  CAACAGAGGG  1080
```

```
CGAGACTCCC  CCGACCGAAG  GAGAGTTGCC  TCCGACCGAA  GAGGTTCCTC  CCACTGAAGA    1140

AGTCACTCCA  CCAACAGAGG  GTGAGACTCC  CCCGACCGAA  GGTGAAGTTC  CTCCAACTGA    1200

GGAGGTTCCT  CCCACTGAAG  AAGTCACTCC  ACCAACAGAG  GGCGAGACTC  CACCCACAGA    1260

AGGTGGGTCC  CTCCAACTGA  AGAGGTCACT  CCACCCACAG  AAGGCGAAAC  TCCCCCGACC    1320

GAAGGAGAGT  TGCCTCCAAC  AGAGGAGGTT  CCTCCCACTG  AGGAAGTCAC  TCCGCCAACA    1380

GAGGGCGAGA  CTCCCCCGAC  CGAAGGAGAG  TTGCCTCCAA  CAGAGGAGGT  TCCTCCCACT    1440

GAGGAAGTCA  CTCCGCCAAC  AGAGGGCGAG  ACTCCCCCGA  CCGAAGGAGA  GTTGCCACCA    1500

ACAGAGGAGG  TTCCTCCCAC  TGAAGAAGTC  ACTCCGCCAA  CAGAGGGCGA  GACTCCCCCG    1560

ACCGAAGGAG  AGTTTCCTCC  AACAGAGGAG  GTACCTCCCA  CTGAAGAAGT  CAGTATAAAA    1620

AAAAAAAAAA  AAAAAAA                                                       1638
```

( 2 ) INFORMATION FOR SEQ ID NO:2:

( i ) SEQUENCE CHARACTERISTICS:
        ( A ) LENGTH: 538 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ala  Arg  Ala  Ile  Ala  Gly  Cys  Asn  Pro  Gly  Asp  Glu  Ser  Pro  Cys  Gln
1              5                        10                       15

Ser  Leu  Val  Leu  Ala  Ser  Trp  Asp  Thr  Leu  Glu  Gln  Arg  Val  Phe  Gln
              20                        25                       30

Ala  Glu  Asp  Gln  Leu  Cys  Glu  Ala  Arg  Glu  Glu  Lys  Glu  Met
              35                        40                       45

Gln  Asn  Gln  Gln  Pro  Ser  Val  Gln  Glu  Pro  Ala  Pro  Pro  Ser  Lys  Thr
         50                        55                       60

Thr  Cys  Thr  Lys  Gly  Arg  Ile  Asp  Thr  Ala  Ala  Val  Leu  Asp  Gly  Ser
65                            70                       75                      80

Gly  Ser  Leu  Ser  Arg  Lys  Asp  Trp  Lys  Ala  Thr  Leu  Glu  Ile  Ala  Asp
                        85                        90                       95

Leu  Phe  Ala  Gly  Ala  Leu  Asn  Ile  Asp  Glu  Ala  Gly  Ser  His  Met  Ser
                100                       105                      110

Val  Val  Arg  Phe  Ala  Thr  Ser  Ala  Thr  Thr  Glu  Trp  Gly  Leu  Leu  Asp
              115                       120                      125

Pro  Val  Ser  Trp  Thr  Pro  Ala  Lys  Leu  Lys  Gln  Arg  Ile  Ser  Arg  Leu
         130                       135                      140

Ser  His  Pro  Arg  Gly  Arg  Thr  Asn  Thr  Pro  Lys  Gly  Leu  Glu  Glu  Ala
145                          150                       155                     160

Tyr  Arg  Ile  Leu  Val  Glu  Ser  Met  Asn  Lys  His  His  Asp  Glu  Asp  Ala
                        165                       170                      175

Glu  Asn  Val  His  Arg  Ile  Leu  Leu  Val  Thr  Thr  Asp  Gly  Cys  Val  Asn
                180                       185                      190

Glu  Trp  Asn  Thr  Arg  Lys  Tyr  Arg  Thr  Ala  Glu  Ala  His  Leu  Lys  Asp
              195                       200                      205

Leu  Leu  Glu  Arg  Phe  Arg  Arg  Leu  Lys  Asn  Leu  His  Ile  Arg  Val  Leu
         210                       215                      220

Ala  Leu  Gly  Ser  Asn  Leu  Cys  Glu  Arg  Glu  Val  Arg  Leu  Ile  Gly  Gly
225                          230                       235                     240

Cys  Arg  Pro  Asp  Gly  Lys  Asp  Ser  Cys  Asp  Asn  Val  Lys  Phe  Thr  Asp
                        245                       250                      255
```

```
Phe  Ser  Ser  Val  Ile  Asp  Glu  Leu  Pro  Gln  Phe  Leu  Glu  Glu  Ile  Cys
               260                      265                     270

Glu  Glu  Val  Glu  Ser  Gly  Val  Pro  Pro  Thr  Leu  Gly  Gly  Asp  Gln  Leu
          275                      280                     285

Pro  Pro  Thr  Glu  Glu  Val  Pro  Pro  Thr  Glu  Glu  Val  Thr  Pro  Pro  Thr
     290                      295                     300

Glu  Gly  Glu  Thr  Pro  Pro  Ala  Glu  Gly  Glu  Leu  Pro  Pro  Thr  Glu  Glu
305                      310                     315                          320

Val  Pro  Pro  Thr  Glu  Glu  Val  Thr  Pro  Pro  Thr  Glu  Gly  Glu  Thr  Pro
                    325                     330                          335

Pro  Thr  Glu  Gly  Glu  Leu  Pro  Pro  Thr  Glu  Glu  Val  Pro  Pro  Thr  Glu
               340                      345                     350

Glu  Val  Thr  Pro  Pro  Thr  Glu  Gly  Glu  Thr  Pro  Pro  Thr  Glu  Gly  Glu
               355                      360                     365

Leu  Pro  Pro  Thr  Glu  Glu  Val  Pro  Pro  Thr  Glu  Glu  Val  Thr  Pro  Pro
     370                      375                     380

Thr  Glu  Gly  Glu  Thr  Pro  Pro  Thr  Glu  Gly  Glu  Val  Pro  Pro  Thr  Glu
385                      390                     395                          400

Glu  Val  Pro  Pro  Thr  Glu  Glu  Val  Thr  Pro  Pro  Thr  Glu  Gly  Glu  Thr
                    405                     410                          415

Pro  Pro  Thr  Glu  Gly  Gly  Ser  Leu  Gln  Leu  Lys  Arg  Ser  Leu  His  Pro
               420                      425                     430

Gln  Lys  Ala  Lys  Leu  Pro  Arg  Pro  Lys  Glu  Ser  Cys  Leu  Gln  Gln  Arg
               435                      440                     445

Arg  Phe  Leu  Pro  Leu  Arg  Lys  Ser  Leu  Arg  Gln  Gln  Arg  Ala  Arg  Leu
          450                      455                     460

Pro  Arg  Pro  Lys  Glu  Ser  Cys  Leu  Gln  Gln  Arg  Arg  Phe  Leu  Pro  Leu
465                      470                     475                          480

Arg  Lys  Ser  Leu  Arg  Gln  Gln  Arg  Ala  Arg  Leu  Pro  Arg  Pro  Lys  Glu
                    485                     490                          495

Ser  Cys  His  Gln  Gln  Arg  Arg  Phe  Leu  Pro  Leu  Lys  Lys  Ser  Leu  Arg
               500                      505                     510

Gln  Gln  Arg  Ala  Arg  Leu  Pro  Arg  Pro  Lys  Glu  Ser  Phe  Leu  Gln  Gln
               515                      520                     525

Arg  Arg  Tyr  Leu  Pro  Leu  Lys  Lys  Ser  Val
               530                      535
```

( 2 ) INFORMATION FOR SEQ ID NO:3:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Leu  Pro  Pro  Thr  Glu  Glu  Val  Pro  Pro  Thr  Glu  Glu  Val  Thr  Pro  Pro
1                   5                        10                          15

Thr  Glu  Gly  Glu  Thr  Pro  Pro  Ala  Glu  Gly  Glu
               20                      25
```

( 2 ) INFORMATION FOR SEQ ID NO:4:

( i ) SEQUENCE CHARACTERISTICS:
        ( A ) LENGTH: 27 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:4:

```
Leu  Pro  Pro  Thr  Glu  Glu  Val  Pro  Pro  Thr  Glu  Glu  Val  Thr  Pro  Pro
 1                  5                        10                            15

Thr  Glu  Gly  Glu  Thr  Pro  Pro  Thr  Glu  Gly  Glu
                20                        25
```

(2) INFORMATION FOR SEQ ID NO:5:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Val  Pro  Pro  Thr  Glu  Glu  Val  Pro  Pro  Thr  Glu  Glu  Val  Thr  Pro  Pro
 1                  5                        10                            15

Thr  Glu  Gly  Glu  Thr  Pro  Pro  Thr  Glu  Gly  Gly
                20                        25
```

(2) INFORMATION FOR SEQ ID NO:6:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Leu  His  Pro  Gln  Lys  Ala  Lys  Leu  Pro  Arg  Pro  Lys  Glu  Ser  Cys  Leu
 1                  5                        10                            15

Gln  Gln  Arg  Arg  Phe  Leu  Pro  Leu  Arg  Lys  Ser
                20                        25
```

(2) INFORMATION FOR SEQ ID NO:7:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Leu  Arg  Gln  Gln  Arg  Ala  Arg  Leu  Pro  Arg  Pro  Lys  Glu  Ser  Cys  Leu
 1                  5                        10                            15

Gln  Gln  Arg  Arg  Phe  Leu  Pro  Leu  Arg  Lys  Ser
                20                        25
```

(2) INFORMATION FOR SEQ ID NO:8:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide -continued (xi) SEQUENCE DESCRIPTION: SEQ ID NO:8:

Leu Arg Gln Gln Arg Ala Arg Leu Pro Arg Pro Lys Glu Ser Cys His
1               5                   10                  15

Gln Gln Arg Arg Phe Leu Pro Leu Lys Lys Ser
            20                  25

(2) INFORMATION FOR SEQ ID NO:9:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:9:

Leu Arg Gln Gln Arg Ala Arg Leu Pro Arg Pro Lys Glu Ser Phe Leu
1               5                   10                  15

Gln Gln Arg Arg Tyr Leu Pro Leu Lys Lys Ser
            20                  25

(2) INFORMATION FOR SEQ ID NO:10:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:10:

Leu Arg Gln Gln Arg Ala Arg Leu Pro Arg Pro Lys Glu Ser Cys Leu
1               5                   10                  15

Gln Gln Arg Arg Phe Leu Pro Leu Lys Lys Ser
            20                  25

(2) INFORMATION FOR SEQ ID NO:11:

(i) SEQUENCE CHARACTERISTICS:
    (A) LENGTH: 27 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Leu Arg Gln Gln Arg Ala Arg Leu Pro Arg Pro Lys Glu Ser Cys Leu
1               5                   10                  15

Gln Gln Arg Arg Phe Leu Pro Leu Arg Lys Ser
            20                  25